US012343270B2

(12) United States Patent
Folan

(10) Patent No.: US 12,343,270 B2
(45) Date of Patent: Jul. 1, 2025

(54) MEDICAL STENTS

(71) Applicant: BOSTON SCIENTIFIC SCIMED INC., Maple Grove, MN (US)

(72) Inventor: Martyn G. Folan, Galway (IE)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 1167 days.

(21) Appl. No.: 17/181,354

(22) Filed: Feb. 22, 2021

(65) Prior Publication Data

US 2021/0196486 A1  Jul. 1, 2021

Related U.S. Application Data

(63) Continuation of application No. 16/100,334, filed on Aug. 10, 2018, now Pat. No. 10,945,866.

(60) Provisional application No. 62/545,179, filed on Aug. 14, 2017.

(51) Int. Cl.
A61F 2/88 (2006.01)
A61F 2/86 (2013.01)
A61F 2/90 (2013.01)

(52) U.S. Cl.
CPC ............... A61F 2/90 (2013.01); A61F 2/86 (2013.01); A61F 2/88 (2013.01); A61F 2230/0091 (2013.01); A61F 2250/0014 (2013.01); A61F 2250/0026 (2013.01); A61F 2250/0067 (2013.01)

(58) Field of Classification Search
CPC ...... A61F 2230/0091; A61F 2250/0014; A61F 2250/0026; A61F 2/86; A61F 2/88; A61F 2/90
See application file for complete search history.

(56) References Cited

U.S. PATENT DOCUMENTS

| 6,083,257 | A  | 7/2000  | Taylor et al.     |
|-----------|----|---------|--------------------|
| 6,249,952 | B1 | 6/2001  | Ding              |
| 6,626,936 | B2 | 9/2003  | Stinson           |
| 7,101,392 | B2 | 9/2006  | Heath             |
| 7,105,018 | B1 | 9/2006  | Yip et al.        |
| 7,594,928 | B2 | 9/2009  | Headley, Jr. et al. |
| 7,691,136 | B2 | 4/2010  | McMorrow          |
| 9,320,592 | B2 | 4/2016  | Wainwright et al. |
| 2009/0254164 | A1 | 10/2009 | Johnson et al.  |
| 2013/0060323 | A1 | 3/2013 | McHugo           |

(Continued)

FOREIGN PATENT DOCUMENTS

| EP | 2045019 A2 | 4/2009 |
| EP | 2045019 B1 | 7/2015 |
| WO | 2013184895 A1 | 12/2013 |

OTHER PUBLICATIONS

International Search Report and Written Opinion dated Nov. 22, 2018 for International Application No. PCT/US2018/046174.

Primary Examiner — William H Matthews
(74) Attorney, Agent, or Firm — Seager, Tufte & Wickhem, LLP

(57) ABSTRACT

An implantable stent may include a braided tubular member formed of braided wires and including radially outward wire segments crossing over and positioned radially outward of radially inward wire segments at a plurality of crossover points. Also, the radially outward wire segments may be coated with a coating and the radially inward wire segments may be uncoated and devoid of the coating.

20 Claims, 24 Drawing Sheets

(56) References Cited

U.S. PATENT DOCUMENTS

2014/0277400 A1* 9/2014 Wainwright ............. A61P 7/02
623/1.42
2016/0235895 A1 8/2016 Costello

* cited by examiner

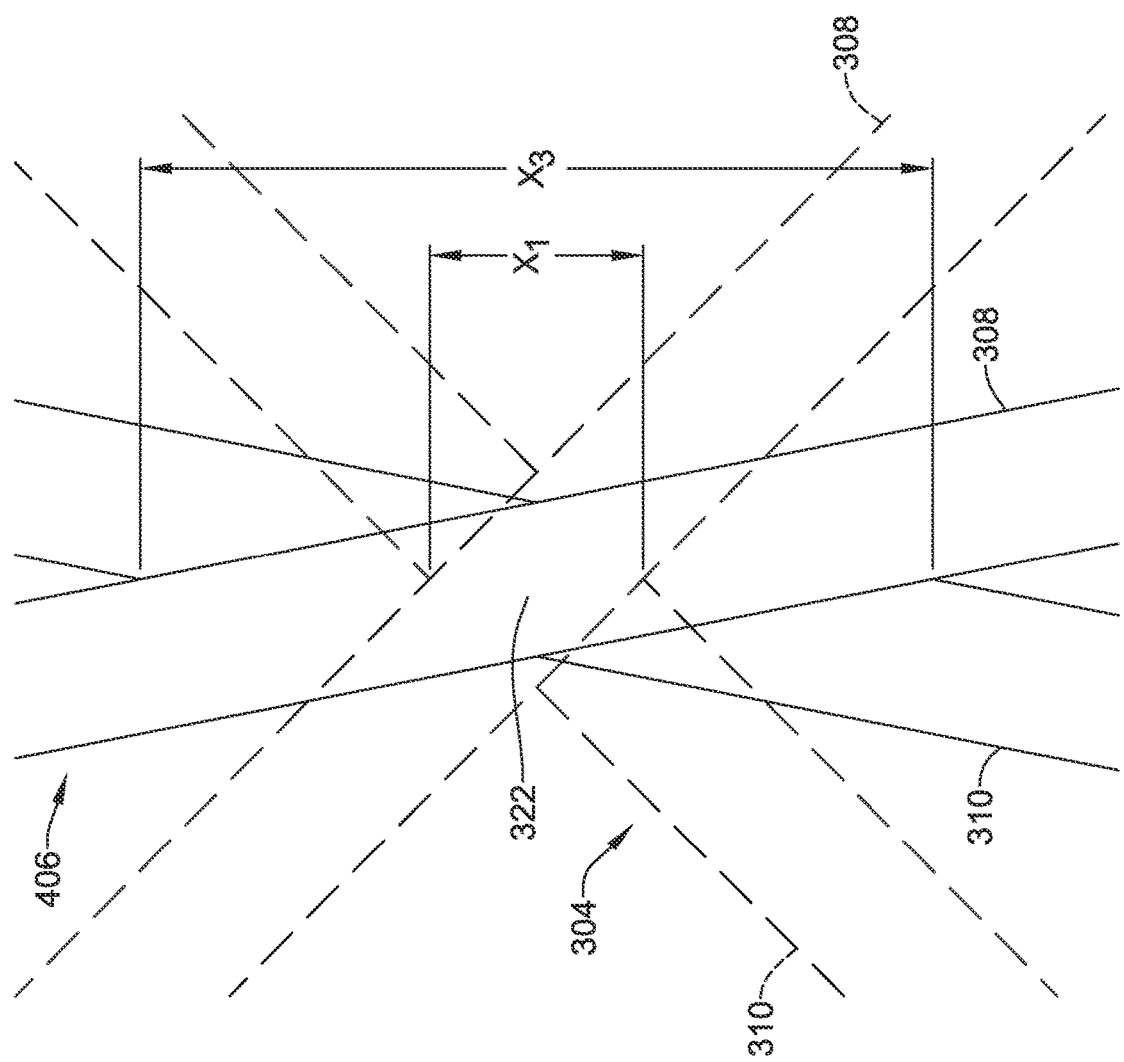

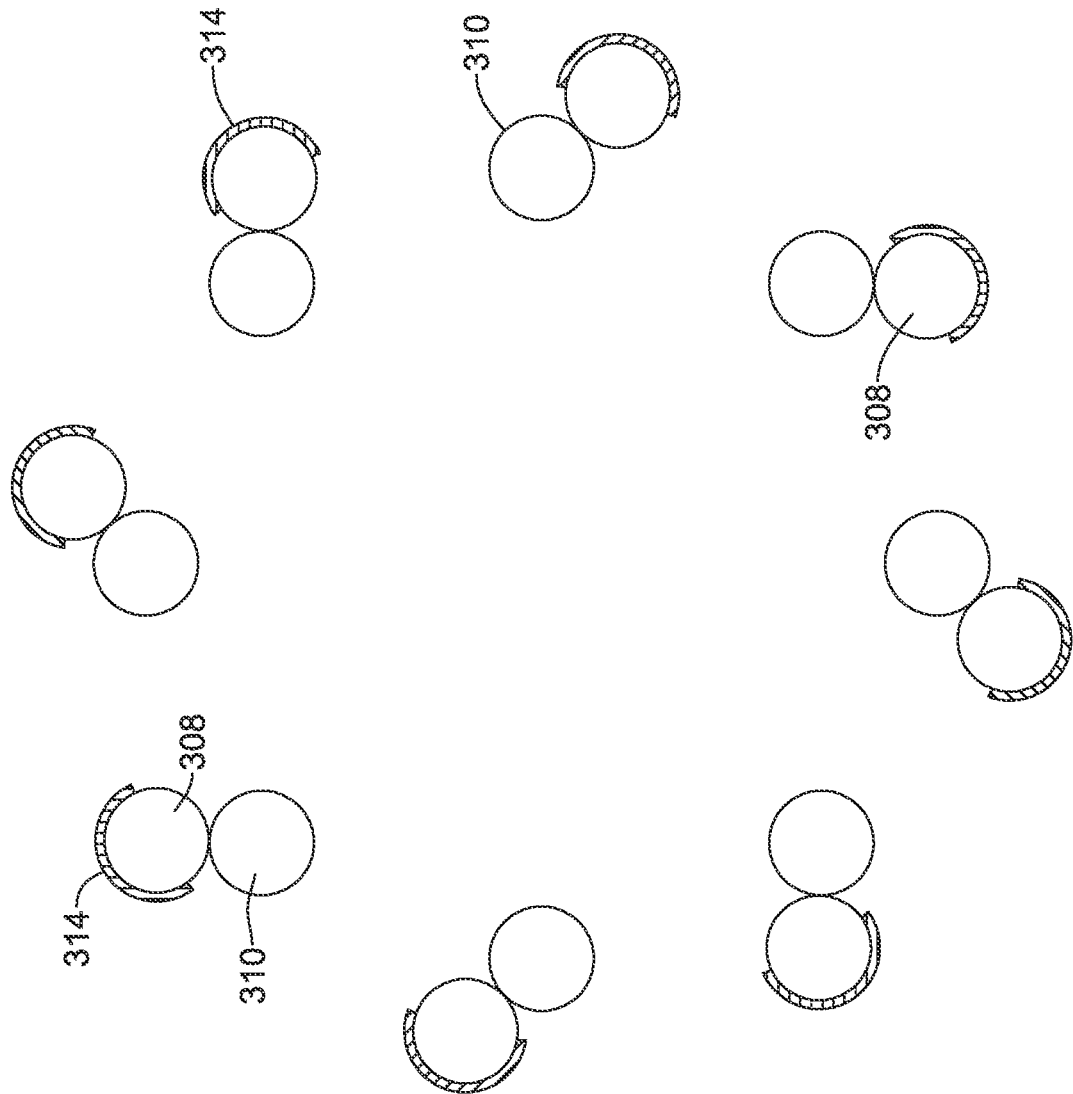

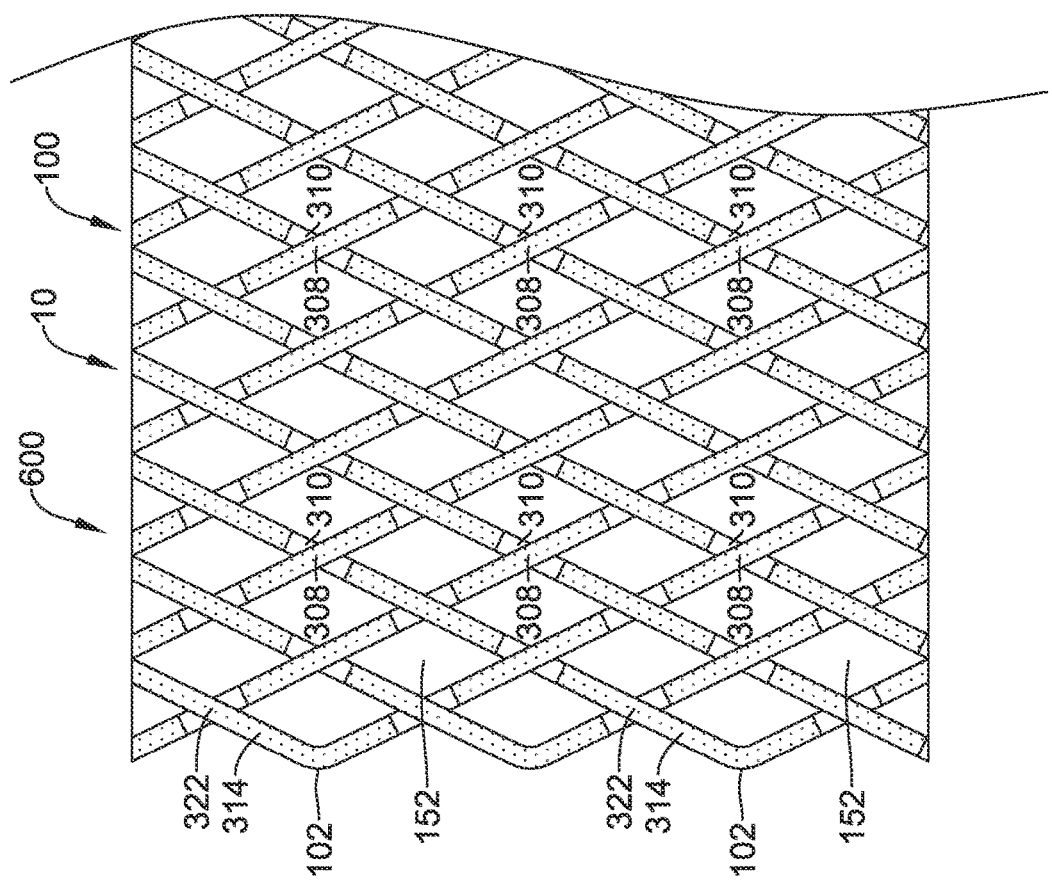

MEDICAL STENTS

CROSS-REFERENCE TO RELATED APPLICATIONS

This application is a continuation of U.S. application Ser. No. 16/100,334 filed Aug. 10, 2018 which claims priority under 35 U.S.C. § 119 to U.S. Provisional Application Ser. No. 62/545,179, filed Aug. 14, 2017, the entirety of which is incorporated herein by reference.

TECHNICAL FIELD

The present disclosure pertains to medical devices, and methods for manufacturing and/or using medical devices. More particularly, the present disclosure pertains to medical stents and methods for manufacturing and/or using medical stents.

BACKGROUND

In medicine, a stent may be a tube comprised of a metal, plastic, or other material or combinations thereof that may be inserted into a lumen of an anatomic body lumen or passageway to keep the lumen or passageway open. There are a wide variety of stents used for different purposes, from expandable coronary, vascular, esophageal, tracheal, colonic, and biliary stents, to stents used to allow the flow of urine between kidney and bladder. Of the known medical stents each has certain advantages and disadvantages. There is an ongoing need to provide alternative medical stents as well as alternative methods for manufacturing and using medical stents.

BRIEF SUMMARY

This disclosure provides design, material, manufacturing method, and use alternatives for medical devices, including delivery devices.

In a first example, an implantable stent may comprise a braided tubular member formed of a plurality of braided wires, the braided tubular member may include a plurality of radially outward wire segments crossing over and positioned radially outward of a plurality of radially inward wire segments at a plurality of crossover points. The radially outward wire segments may be coated with a coating and the radially inward wire segments may be uncoated and may be devoid of the coating.

Alternatively or additionally to any of the examples above, in another example, each of the plurality of braided wires may include radially outward wire segments alternating with radially inward wire segments.

Alternatively or additionally to any of the examples above, in another example, the radially outward wire segments may be configured to pivot relative to the plurality of radially inward wire segments at the crossover points as the braided tubular member is radially expanded and radially contracted.

Alternatively or additionally to any of the examples above, in another example, the plurality of braided wires may define open cells therebetween and the coating may not extend across the open cells between adjacent wires.

Alternatively or additionally to any of the examples above, in another example, an uncoated length of the radially inward wire segments may be greater than a length of the radially inward wire segments contacting the radially outward wire segments at the crossover points when the braided tubular member is in a nominally deployed state.

Alternatively or additionally to any of the examples above, in another example, the braided tubular member may be radially compressible from the nominally deployed state to a radially contracted state. A length of the radially inward wire segments contacting the radially outward wire segments at the crossover points in the radially contracted state may be greater than the length of the radially inward wire segments contacting the radially outward wire segments at the crossover points when the braided tubular member is in the nominally deployed state.

Alternatively or additionally to any of the examples above, in another example, the radially contracted state may be determined based on a pivot angle between adjacent wire segments at the crossover points.

Alternatively or additionally to any of the examples above, in another example, the pivot angle may have a value between 0° and 45°.

Alternatively or additionally to any of the examples above, in another example, an uncoated length of the radially inward wire segments may be greater than a diameter of the radially outward wire segments at the crossover points.

In another example, an implantable stent may comprise a tubular member that may be formed of a plurality of braided wires forming a braid pattern including a plurality of crossover points and the first and second wire segments of the braided wires may intersect at each crossover point such that the first wire segment may cross over and radially outward of the second wire segment while the second wire segment may cross under and radially inward of the first wire segment. A coating may be disposed only on the first wire segments which may cross over and may be radially outward of the second wire segments and the second wire segments may cross under and radially inward of the first wire segments may be devoid of the coating.

Alternatively or additionally to any of the examples above, in another example, each of the plurality of braided wires may include a plurality of first wire segments that may include the coating alternating with a plurality of second wire segments that may be devoid of the coating along a length of the wire.

Alternatively or additionally to any of the examples above, in another example, the plurality of braided wires may include a first wire, a second wire, a third wire, and a fourth wire and the first and second wires may extend parallel to one another in a first helical direction, and the third and fourth wires may extend parallel to one another in an opposite, second helical direction. The first wire may cross over and radially outward of the third wire at a first crossover point and may cross under and radially inward of the fourth wire at a second crossover point. The second wire may cross under and radially inward of the third wire at a third crossover point and may cross over and radially outward of the fourth wire at a fourth crossover point. A first portion of the first wire may form first wire segments coated with the coating and a second portion of the first wire may form second wire segments devoid of the coating. A first portion of the second wire may form first wire segments coated with the coating and a second portion of the second wire may form second wire segments devoid of the coating. A first portion of the third wire may form first wire segments coated with the coating and a second portion of the third wire may form second wire segments devoid of the coating. A first portion of the fourth wire may form first wire segments coated with the coating and a second portion of the fourth wire may form second wire segments devoid of the coating.

Alternatively or additionally to any of the examples above, in another example, the first wire, the second wire, the third wire, and the fourth wire may define an open cell therebetween and the coating may not extend across the open cell.

Alternatively or additionally to any of the examples above, in another example, the first wire, the second wire, the third wire, and the fourth wire may be configured to pivot at the first, second, third, and fourth crossover points and axially expand and may geometrically alter an appearance of the open cell.

Alternatively or additionally to any of the examples above, in another example, the first wire and the third wire may not slide relative to each other at the first crossover point, the first wire and the fourth wire may not slide relative to each other at the second crossover point, the second wire and the third wire may not slide relative to each other at the third crossover point, and the second wire and the fourth wire may not slide relative to each other at the fourth crossover point.

Alternatively or additionally to any of the examples above, in another example, the coating may include a therapeutic agent.

In another example, a method of selectively coating portions of an expandable stent, may comprise applying an axial force to a braided tubular member to change an axial length of the braided tubular member from a length of the braided tubular member in a nominally deployed state and the braided tubular member may include radially outward wire segments crossing over and located radially outward of radially inward wire segments of the braided tubular member at a plurality of crossover points. Applying the axial force may change an angle between the radially outward wire segments and the radially inward wire segments of the braided tubular member at the crossover points. Thereafter, applying a coating to the radially outward wire segments while avoiding coating the radially inward wire segments.

Alternatively or additionally to any of the examples above, in another example, an uncoated length of the radially inward wire segments may be greater than a length of the radially inward wire segments contacting the radially outward wire segments at the crossover points when in the nominally deployed length.

Alternatively or additionally to any of the examples above, in another example, the braided tubular member may include a plurality of braided wires and each of the plurality of braided wires may include radially outward wire segments alternating with radially inward wire segments.

Alternatively or additionally to any of the examples above, in another example, the coating may be applied when the angle has a value between 5° to 45° or between 150° to 175°.

BRIEF DESCRIPTION OF THE DRAWINGS

The disclosure may be more completely understood in consideration of the following detailed description in connection with the accompanying drawings, in which:

FIG. 4C is an enlarged view of a crossover point of intersecting wires of the braided tubular member illustrating movement of the intersecting wires between a nominally deployed state (dashed lines) and an axially contracted state (solid lines).

FIG. 4D depicts a cross sectional view of the braided tubular member of the stent of FIG. 1A taken along line 4D-4D of FIG. 4A.

FIGS. 6A-6C depict the braided tubular member of the stent in various states after application of the coating.

Figure 1A:
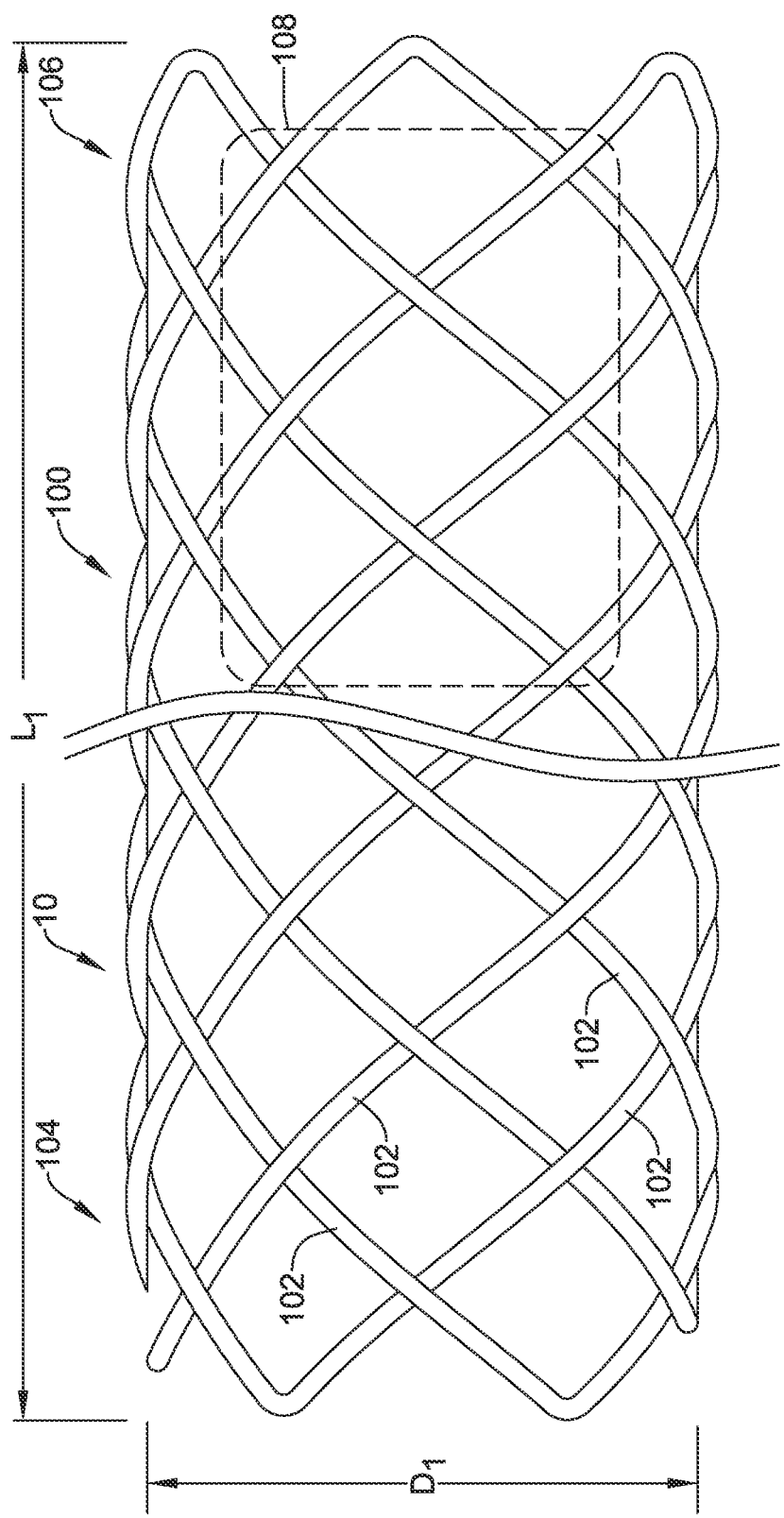
FIG. 1A depicts an exemplary stent including a braided tubular member formed from braided wires in a nominally deployed state.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

FIG. 1A depicts an exemplary stent 10 including a braided tubular member 100 formed from braided wires 102 in a nominally deployed state (i.e., an equilibrium state without external forces acting on the stent). In some cases, the braided tubular member 100 may have a diameter $D_1$ and a length $L_1$ in the nominally deployed state. In certain embodiments, the braided wires 102 may have a first set of wire segments that extend parallel to one another in a first helical direction and a second set of wire segments that extend parallel to one another in a second helical direction, opposite of the first helical direction. As such, the first set of wire segments and the second set of wire segments may cross or intersect multiple times at the crossover points to form a braid pattern. In some cases, the braid pattern may be uneven or non-uniform because the spacing between the individual wire segments from either set of wire segments may vary or the angle at which the wire segments cross may vary. In some instances the braid pattern may be in a one-under and one-over braiding configuration in which a single wire segment extending in the first helical direction intersects a single wire segment extending in the second helical direction at each crossover point. In the one-under and one-over braiding configuration, a wire segment from the first set of wire segment may be located above (radially outward of) a first wire segment from the second set of wire segments at a first crossing (i.e., crossover point), then below a second wire segment from the second set of wire segments at a second crossing (i.e., crossover point), then above a third wire segment from the second set of wire segments at a third crossing (i.e., crossover point), and continue in this alternating pattern from a first end 104 of the braided tubular member 100 to a second end 106 of the braided tubular member 100. Moreover, the other wires from the braided wires 102 may also be braided in this alternating pattern from the first end 104 to the second end 106. Furthermore, each wire of the braided wires 102 may be observed as a plurality of wire segments. As such, in the one-under and one-over braiding configuration, each wire may be comprised of alternating radially outward wire segments (i.e., segments of the wire extending radially outward of another wire at a crossover point) and radially inward wire segments (i.e., segments of the wire extending radially inward of another wire at a crossover point). Thus, the radially outward wire segments may be positioned radial outward of the radially inward wire segments at the crossover points.

Figure 1B:
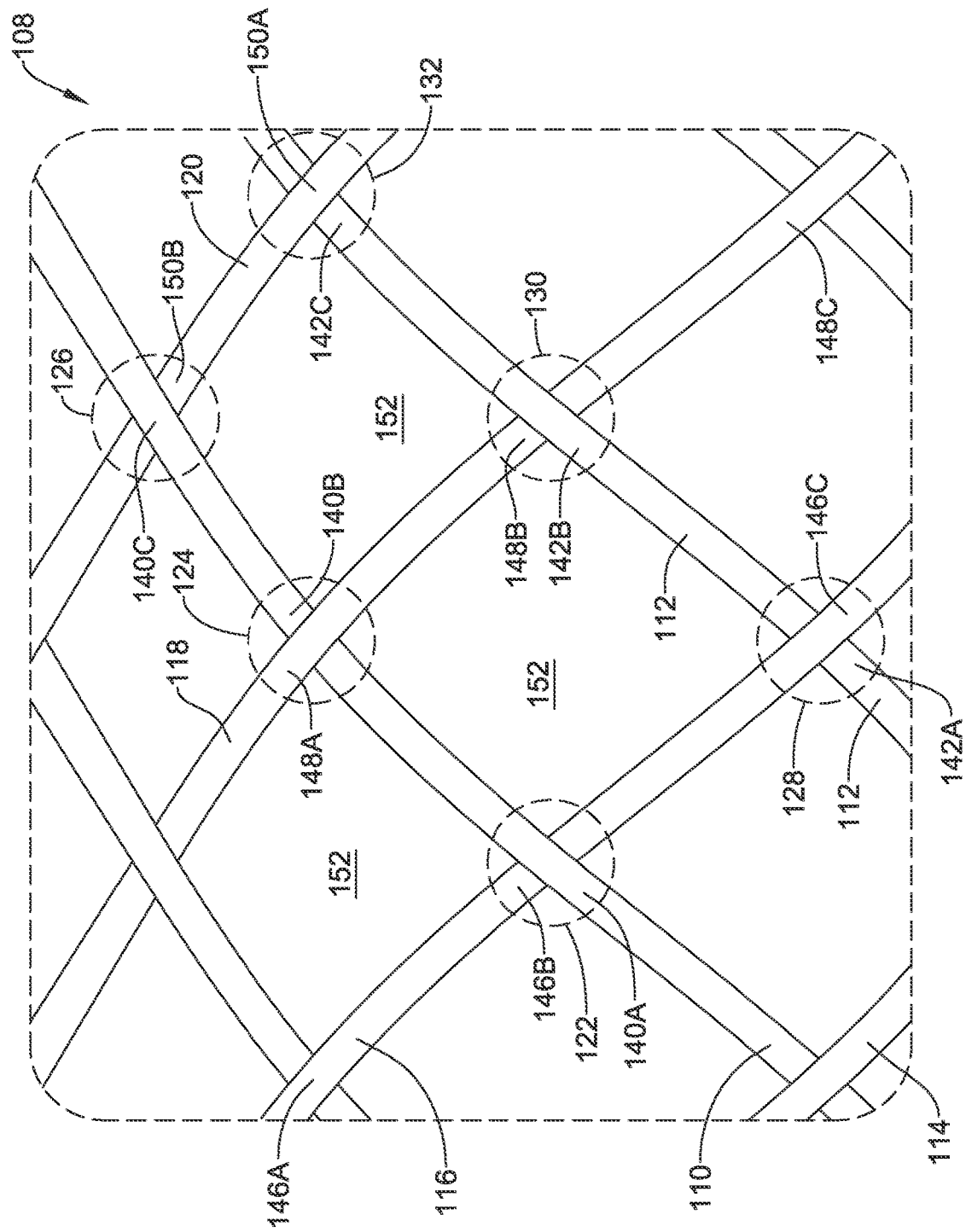
FIG. 1B depicts an enlarged view of a section of the braided tubular member of the stent of FIG. 1A.

Turning to FIG. 1B, an enlarged view of a section 108 of the braided tubular member 100 is depicted. The section 108 may include wires 110, 112, 114, 116, 118, and 120. As shown, wire 110 crosses over wire 116 at crossover point 122, crosses under wire 118 at crossover point 124, and crosses over wire 120 at crossover point 126. Accordingly, wire 110 includes radially outward wire segments 140A, 140C and radially inward wire segment 140B between the radially outward wire segments 140A, 140C. Wire 112 crosses under wire 116 at crossover point 128, crosses over wire 118 at crossover point 130, and crosses under wire 120 at crossover point 132. Accordingly, wire 112 includes radially inward wire segments 142A, 142C and radially outward wire segment 142B between the radially inward wire segments 142A, 142C. Wire 116 crosses under wire 110 at crossover point 122 and crosses over wire 112 at crossover point 128. Accordingly, wire 116 includes radially outward wire segments 146A, 146C and radially inward wire segment 146B between the radially outward wire segments 146A, 146C. Also, wire 118 crosses over wire 110 at crossover point 124 and crosses under wire 112 at crossover point 130. Accordingly, wire 118 includes radially outward wire segments 148A, 148C and radially outward wire segment 148B between the radially outward wire segments 148A, 148C. Finally, wire 120 crosses over wire 112 at crossover point 132 and crosses under wire 110 at crossover point 126. Accordingly, wire 120 includes radially outward wire segment 150A and radially inward wire segment 150B. As such, the braided tubular member 100 may include and be comprised of a plurality of radially outward wire segments (e.g., radially outward wire segments 140A, 140C, 142B, 146A, 146C, 148A, 148C, and 150A) crossing over and positioned radially outward of a plurality of radially inward wire segments (e.g., radially inward wire segments 140B, 142A, 142C, 146B, 148B, and 150B) at a plurality of crossover points (e.g., crossover points 122-132). In various embodiments, the one-under and one-over configuration of the wires 110-120 may define a plurality open cells (e.g., open cell 152). Open cells 152 may be openings through the tubular wall of the braided tubular member 100 from an outer surface to an inner surface of the braided tubular member 100. The open cells 152 may have a parallelogram shape, having upper apexes, lower apexes, and side apexes formed by the crossover points (e.g., crossover points 122-132).

The braided tubular member 100 is not limited to the one-under and one-over configuration. In some alternate configurations, the wires 102 may be braided in a two-under and a two-over pattern. Other braiding patterns known in the art may also be suitably used. Further, in some cases, the wires 102 may be paired with one another and braided by using each pair of wires in a one-under and one-over pattern. The pairs of wires may be the same or may be different (e.g., may have the same or different dimensions, shapes and/or materials of construction). Moreover, the pairs of wires may suitably be braided in other braided patterns, such as but not limited to, for example, the two-under and two-over pattern.

According to various embodiments, the wires 102 may be made from any suitable implantable material, including without limitation nickel-titanium alloy (e.g., nitinol), stainless steel, cobalt-based alloy such as Elgiloy®, platinum, gold, titanium, tantalum, niobium, polymeric materials and combinations thereof. Useful polymeric materials may include, for example, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, natural silk, polyvinyl chloride, polytetrafluoroethylene, including expanded polytetrafluoroethylene (ePTFE), fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, and copolymers and combinations thereof. Further, useful and nonlimiting examples of polymeric stent materials include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly(phosphate ester) and the like. Wires made from polymeric materials may also include radiopaque materials, such as metallic-based powders, particulates or pastes which may be incorporated into the polymeric material. For example, the radiopaque material may be blended with the polymer composition from which the polymeric wire is formed, and subsequently fashioned into the stent as described herein. Alternatively, the radiopaque material may be applied to the surface of the metal or polymer stent. In either embodiment, various radiopaque materials and their derivatives may be used including, without limitation, bismuth, barium and its derivatives such as barium sulphate, tantulaum, tungsten, gold, platinum and titanium, to name a few. Additional useful radiopaque materials may be found in U.S. Pat. No. 6,626,936, which is herein incorporated in its entirety by reference. Metallic complexes useful as radiopaque materials are also contemplated. The braided tubular member 100 may be selectively made radiopaque at desired areas along the wire or may be fully radiopaque, depending on the desired end-product and application. Further, the wires 102 may have an inner core of tantalum, gold, platinum, iridium or combinations thereof and an outer member or layer of nitinol to provide a composite wire for improved radiopacity or visibility. In some cases, the inner core may be platinum and the outer layer may be nitinol. In some cases, the inner core of platinum may represent about at least 10% of the wire based on the overall cross-sectional percentage. Moreover, nitinol that has not been treated for shape memory such as by heating, shaping and cooling the nitinol at its martensitic and austenitic phases, may also useful as the outer layer. Further details of such composite wires may be found in U.S. Pat. No. 7,101,392, the contents of which is incorporated herein by reference.

Figure 2:
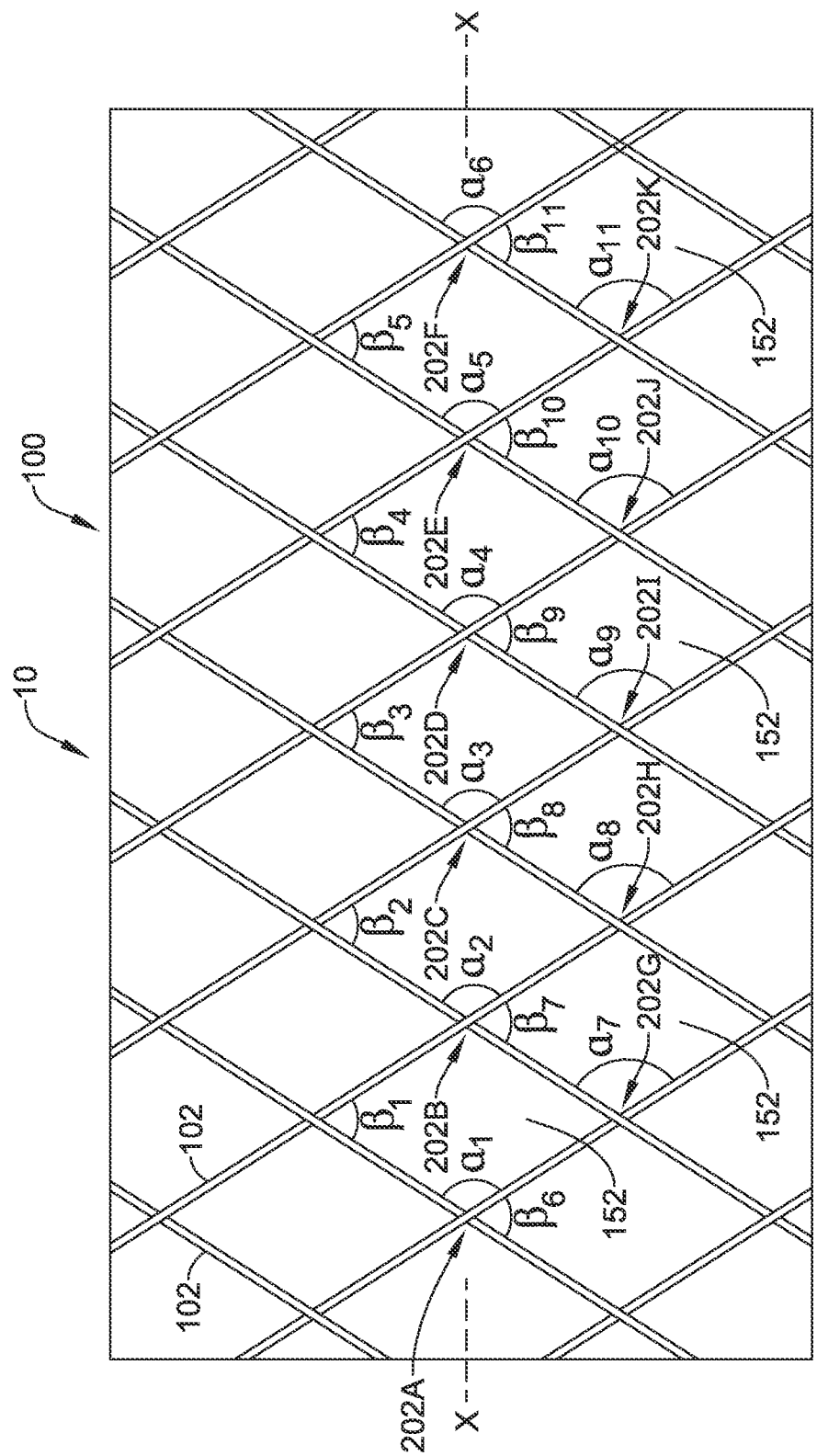
FIG. 2 depicts an example of a radially expandable/contractible function of the braided tubular member of the stent of FIG. 1A.

FIG. 2 depicts an example of a radially expandable/contractible function of the braided tubular member 100 of the stent 10. As can be seen, FIG. 2 depicts a section of the braided tubular member 100 in the one-under and one-over configuration. In some examples, the section depicted in FIG. 2 may be the same section 108 described in regard to FIG. 1B. However, in other examples, the section depicted in FIG. 2 may be another section of the braided tubular member 100.

As described above, the braided wires 102 may cross multiple times with one another at crossover points (e.g., crossover points 122-132, from FIG. 1B). These crossover points may also function as pivot points (e.g., pivot points 202a-202k) and the radially outward wire segments (e.g., radially outward wire segments from FIG. 1B) may pivot relative to the radially inward wire segments (e.g., radially inward wire segments from FIG. 1B) when an applied forces is applied to the stent 10 such that the braided tubular member 100 is axially elongated or axially contracted. For example, an axial force (i.e., a force resulting in axial elongation or axial contraction of the braided tubular member 100) may be applied to the braided tubular member 100. In some cases, the axial force may be applied to the first 104 and second 106 ends (shown in FIG. 1A) of the braided tubular member 100. When the axial force is applied, the braided wires 102 may pivot about the pivot points $202a$-$202k$ and alter pivot angles $\alpha_1$-$\alpha_{11}$. In some cases, as shown, the pivot angles $\alpha_1$-$\alpha_{11}$ may be the measured angles bisected by a longitudinal axis X (or a line segment parallel to the longitudinal axis X) of the braided tubular member 100. In certain embodiments, when the braided tubular member 100 is in the nominally deployed state, the measured angles $\alpha_1$-$\alpha_{11}$ may range from about 75° to about 135°, from about 80° to about 120°, about 90° to about 110°, or about 90°, about 100°, or about 110°. Moreover, the pivoting of the braided wires 102 at the pivot points $202a$-$202k$ may alter the shape of open cells 152. In some examples, an applied force that axially elongates the braided tubular member 100, and thus moves the first 104 and second 106 ends apart, may decrease the pivot angles $\alpha_1$-$\alpha_{11}$. In this regard, by decreasing the pivot angles $\alpha_1$-$\alpha_{11}$, the diameter $D_1$ (from FIG. 1A) of the braided tubular member 100 may be radially contracted and the length $L_1$ (from FIG. 1A) of the braided tubular member 100 may be axially elongated from its nominally deployed state to an axially elongated state (also considered a radially contracted state). In certain embodiments, when the braided tubular member 100 is in the axially elongated state, the measured angles $\alpha_1$-$\alpha_{11}$ may be less than or equal to 45°, less than or equal to 35°, or less than or equal to 25°. In some instances, the measured angles $\alpha_1$-$\alpha_{11}$ may be in the range from about 0° to less than or equal to 45°, about 0° to less than or equal to 35°, about 0° to less than or equal to 25°, about 5° to less than or equal to 45°, about 5° to less than or equal to 35°, or about 5° to less than or equal to 25°. In some examples, an applied force that axially contracts the braided tubular member 100, and thus moves the first 104 and second 106 ends together, may increase the pivot angles $\alpha_1$-$\alpha_{11}$. In this regard, by increasing the pivot angles $\alpha_1$-$\alpha_{11}$, the diameter $D_1$ may be radially expanded and the length $L_1$ may be axially contracted from its nominally deployed state to an axially contracted state (also considered a radially expanded state). In certain embodiments, when the braided tubular member 100 is in the axially contracted state, the measured angles $\alpha_1$-$\alpha_{11}$ may be greater than or equal to 150°, greater than or equal to 155°, or greater than or equal to 160°. In some instances, the measured angles $\alpha_1$-$\alpha_{11}$ may be in the range from greater than or equal to 150° to about 180°, greater than or equal to 155° to about 180°, greater than or equal to 160° to about 180°, greater than or equal to 150° to about 175°, greater than or equal to 155° to about 175°, or greater than or equal to 160° to about 175°.

Alternatively and additionally, the effects of the applied axial force may be viewed with respect to pivot angles $\beta_1$-$\beta_{11}$. Angles $\beta_1$-$\beta_{11}$ may be supplementary angles to angles $\alpha_1$-$\alpha_{11}$. In some cases, as shown, the pivot angles $\beta_1$-$\beta_{11}$ may be the measured angles in relation to a circumferential direction (or a line segment perpendicular to the longitudinal axis X) of the braided tubular member 100. Moreover, the pivoting of the braided wires 102 at the pivot points 202a-202k may once again, alter the shape of open cells 152. In certain embodiments, when the braided tubular member 100 is in the nominally deployed state, the measured angles $\beta_1$-$\beta_{11}$ may range from about 45° to about 105°, from about 60° to about 100°, about 70° to about 90°, or about 70°, about 80°, or about 90°. In some examples, the applied force that axially elongates the braided tubular member 100, and thus moves the first 104 and second 106 ends apart, may increase the pivot angles $\beta_1$-$\beta_{11}$. In this regard, by increasing the pivot angles $\beta_1$-$\beta_{11}$, the diameter $D_1$ of the braided tubular member 100 may be radially contracted and the length $L_1$ of the braided tubular member 100 may be axially elongated from its nominally deployed state to the axially elongated state (or radially contracted state). In certain embodiments, when the braided tubular member 100 is in the axially elongated state, the measured angles $\beta_1$-$\beta_{11}$ may be greater than or equal to 135°, greater than or equal to 145°, or greater than or equal to 155°. In some instances, the measured angles $\beta_1$-$\beta_{11}$ may be in the range from greater than or equal to 135° to about 180°, greater than or equal to 145° to about 180°, greater than or equal to 155° to about 180°, greater than or equal to 135° to about 175°, greater than or equal to 145° to about 175°, or greater than or equal to 155° to about 175°. In some examples, an applied force that axially contracts the braided tubular member 100, and thus moves the first 104 and second 106 ends together, may decrease the pivot angles $\beta_1$-$\beta_{11}$. In this regard, by decreasing the pivot angles $\beta_1$-$\beta_{11}$, the diameter $D_1$ may be radially expanded and the length $L_1$ may be axially contracted from its nominally deployed state to the axially contracted state (or radially expanded state). In certain embodiments, when the braided tubular member 100 is in the axially contracted state, the measured angles $\beta_1$-$\beta_{11}$ may be less than or equal to 30°, less than or equal to 25°, or less than or equal to 20°. In some instances, the measured angles $\beta_1$-$\beta_{11}$ may be in the range from about 0° to less than or equal to 30°, about 0° to less than or equal to 25°, about 0° to less than or equal to 20°, about 5° to less than or equal to 30°, about 5° to less than or equal to 25° to about 175°, about 5° to less than or equal to 20°.

In certain embodiments, the braided tubular member 100 may maintain structural integrity even when the axial forces are applied and the braided tubular member 100 undergoes geometric changes. In some cases, when the braided tubular member 100 undergoes these geometric changes, by maintaining structural integrity, the braided wires 102 may be configured to exhibit pivotal motion about the pivot points 202a-202k, but do not slide, shift, or drift along an intersecting wire 102. This allows the location of a radially outward wire segment to be substantially constant relative to the radially inward wire segment where it crosses over at its respective crossover point. Maintaining the crossover points at a constant location along the length of the wire segments may prevent a selectively applied coating that may be disposed on the braided tubular member 100, as described herein. In some instances, the braided wires 102 may be non-inter-locking in the braided configuration. Such non-interlocking braiding configurations may exclude, inter-twisting, inter-looping, inter-engaging and the like at the crossover points. However, in some cases, the braided wires 102 may be braided or woven in an interlocking manner.

Figure 3A:
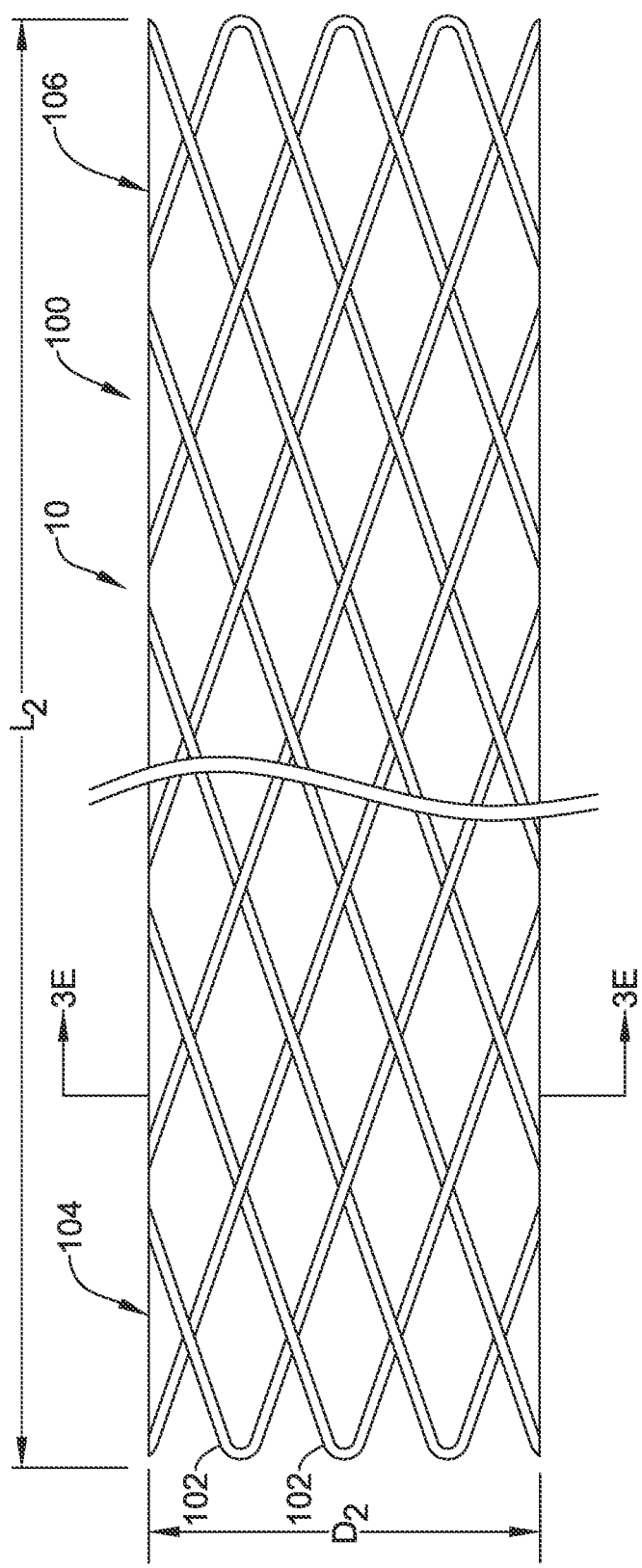
FIG. 3A depicts the exemplary stent of FIG. 1A in an axially elongated state.

FIG. 3A depicts the exemplary braided tubular member 100 of the stent 10 in an axially elongated state (or radially contracted state). In some cases, the braided tubular member 100 may have been adjusted into the axially elongated state using an applied force that axially moves the first 104 and second 106 ends apart. The applied force moves the braided tubular member 100 from its nominally deployed state (i.e., equilibrium state without externally applied forces) to the axially elongated state. As shown, the braided tubular member 100 has been radially contracted and the diameter of the braided tubular member 100 has decreased from diameter $D_1$ at the nominally deployed state to diameter $D_2$ at the axially elongated state, and the length of the braided tubular member 100 has increased from length $L_1$ at the nominally deployed state to $L_2$ at the axially elongated state.

Figure 3B:
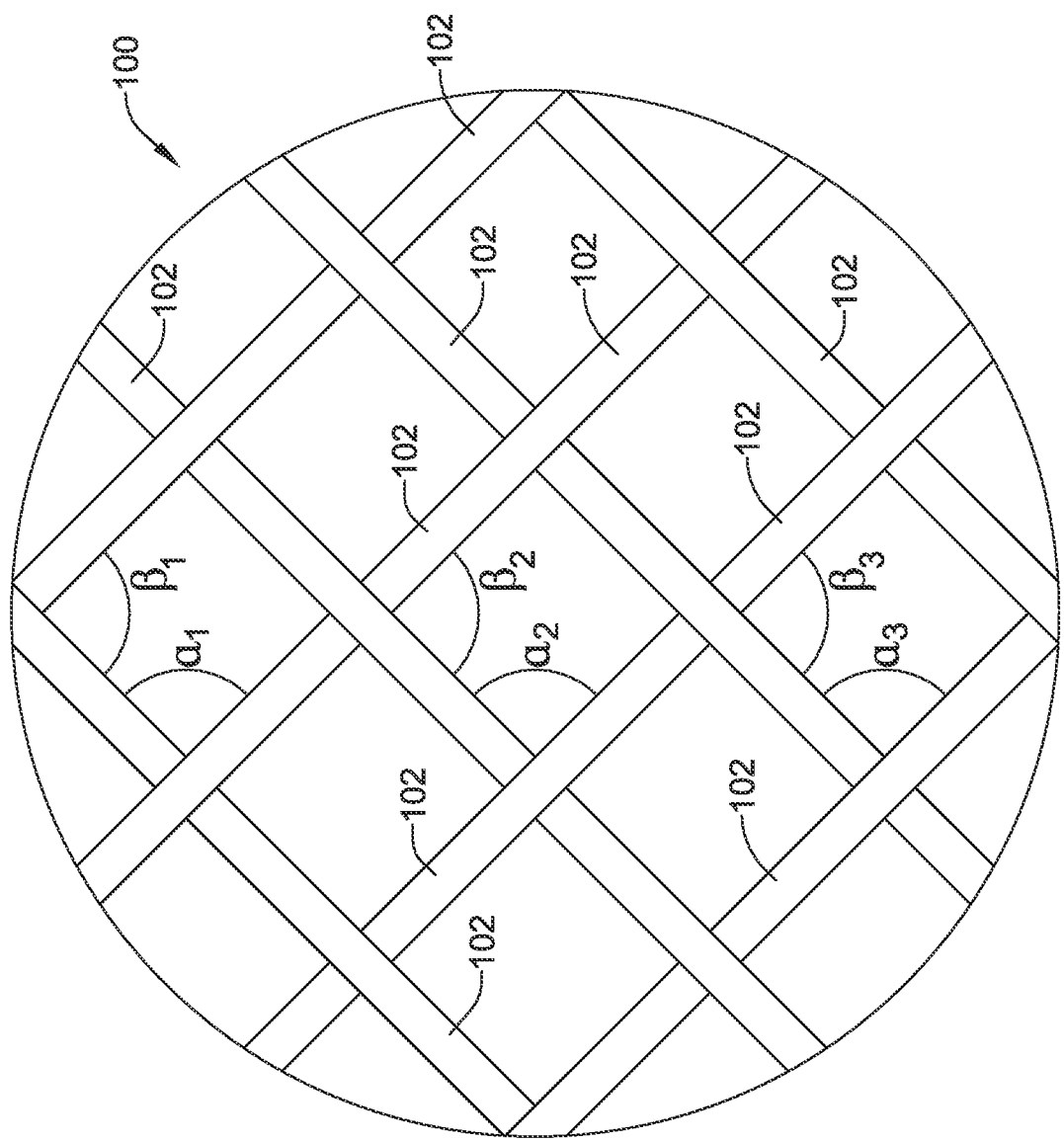
FIG. 3B depicts an enlarged view of the braided tubular member of the stent of FIG. 1A in a nominally deployed state.
Figure 3C:
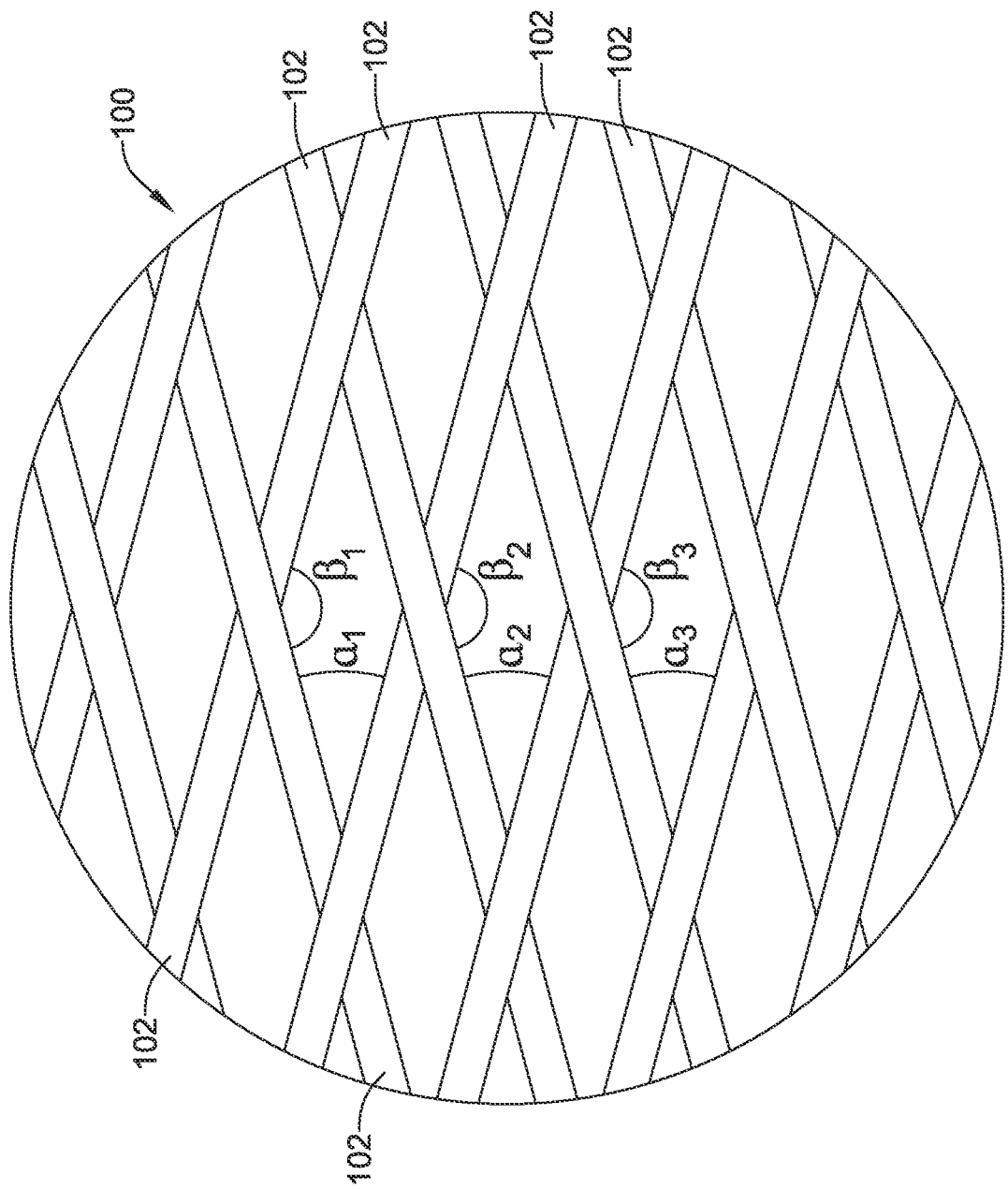
FIG. 3C depicts an enlarged view of the braided tubular member of the stent of FIG. 1A in an axially elongated state.

FIG. 3B depicts an enlarged view of a portion of the braided tubular member 100 in the nominally deployed state as described in regard to FIG. 1A. FIG. 3C depicts an enlarged view of a portion of the braided tubular member 100 in the axially elongated state as described in FIG. 3A. As shown, the pivot angles $\alpha_1$-$\alpha_3$ have decreased from their nominally deployed measured values in FIG. 3B to their axially elongated state measured values in FIG. 3C. Also, the pivot angles $\beta_1$-$\beta_3$ have increased from their nominally deployed measured values in FIG. 3B to their axially elongated state measured values in FIG. 3C.

Figure 3D:
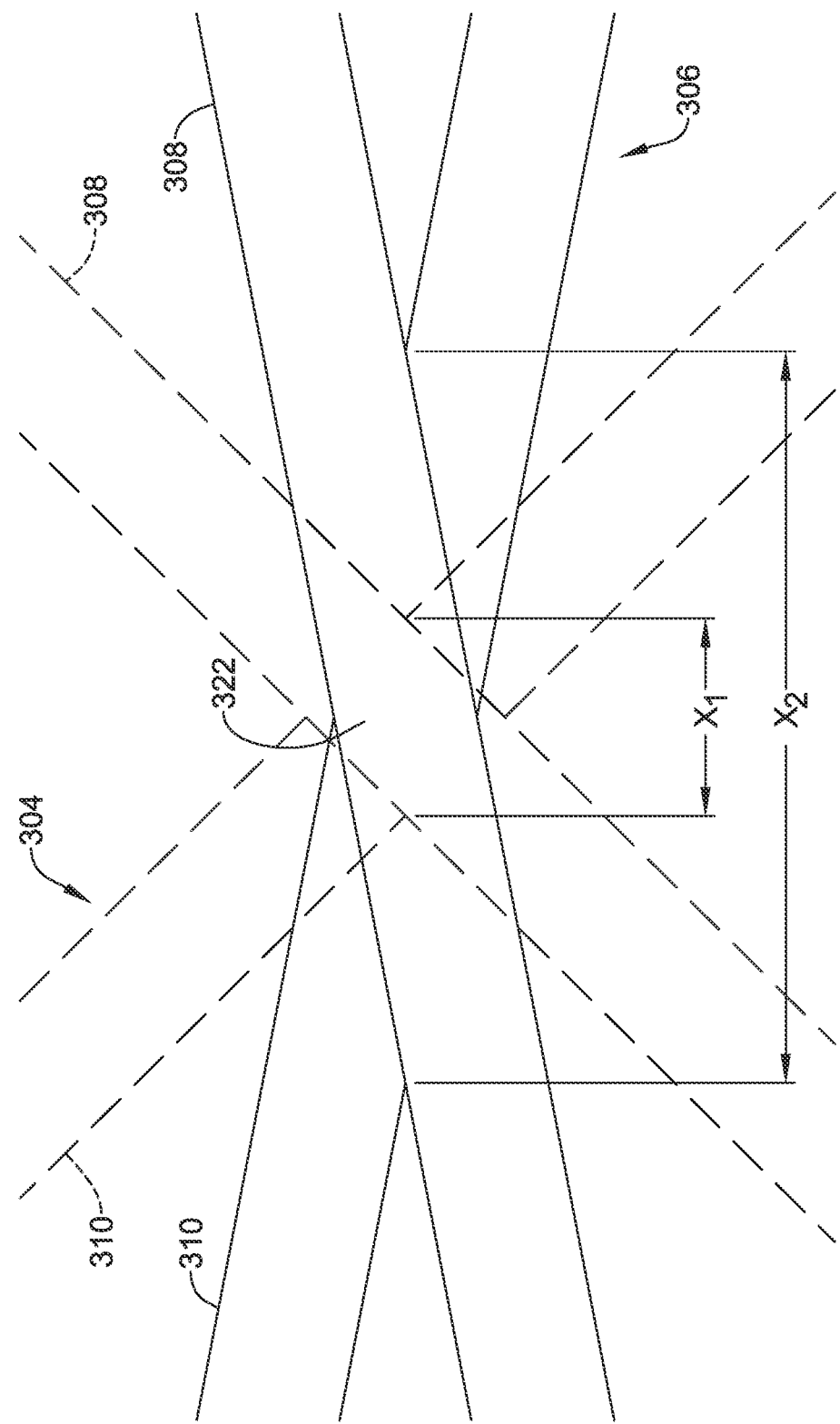
FIG. 3D is an enlarged view of a crossover point of intersecting wires of the braided tubular member illustrating movement of the intersecting wires between a nominally deployed state (dashed lines) and an axially elongated state (solid lines).

FIG. 3D is an enlarged view of a crossover point of intersecting wires of the braided tubular member 100 illustrating movement of the intersecting wires 102 between a nominally deployed state (dashed lines) and an axially elongated state (solid lines). The view 304 (dashed lines) depicts the braided tubular member 100 in the nominally deployed state and the view 306 (solid lines) depicts the braided tubular member 100 in the axially elongated state. As shown, the view 304 is superimposed (illustrated using dashed lines) onto the view 306 with a common pivot point at the crossover point 322 of a radially outward wire segment 308 of a wire 102 and a radially inward wire segment 310 of a wire 102. Moreover, FIG. 3D is used to illustrate one radially outward wire segment 308 and one radially inward wire segment 310. In the nominally deployed state shown in view 304, the radially outward wire segment 308 covers, goes over, is above, and/or is radially outward of and contacts a length $X_1$ of the radially inward wire segment 310. However, in the axially elongated state shown in view 306 the radially outward wire segment 308 covers, goes over, is above, and/or is radially outward of and contacts a length $X_2$ of the radially inward wire segment 310. As can be seen, the length of $X_2$ of the radially inward wire segment 310 in contact with the radially outward wire segment 308 in the axially elongated state may be greater than the length $X_1$ of the radially inward wire segment 310 in contact with the radially outward wire segment 308 in the nominally deployed state. As described in further detail below, the uncoated portions of the wires (e.g., sections of each wire that are not coated, and thus devoid of a coating) may have a length greater than or equal to the length $X_2$ that the radially inward wire segment 310 is in contact with the radially outward wire segment 308 in the axially elongated state to ensure the outward wire segment 308 does not contact or rub across the coating on the coated portion of the wire forming the inward wire segment 310 on either side of the crossover point.

Figure 3E:
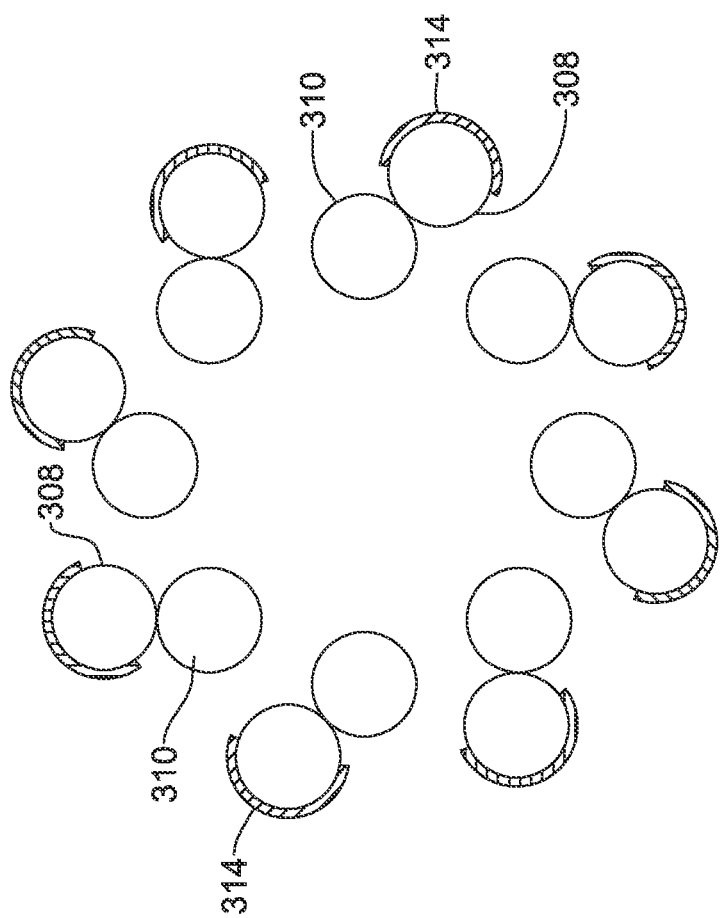
FIG. 3E depicts a cross sectional view of the braided tubular member of the stent of FIG. 1A taken along line 3E-3E of FIG. 3A.

FIG. 3E depicts a cross-sectional view of the braided tubular member 100 in the axially elongated state taken along line 3E-3E of FIG. 3A. As discussed above, the radially outward wire segment 308 may reside radially outward of the radially inward wire segment 310 at each crossover point. As shown in FIG. 3E, select portions of the braided tubular member 100 may be coated with a coating 314 applied directly thereto. For example, the radially outward wire segments 308 may be coated with a coating 314 using such techniques as roll coating, dot matrix print coating, electrospinning coating, and spray coating, for example, while leaving an uncoated length of the inward wire segments 310 at each crossover point 122. In certain embodiments, when the coating 314 is applied to the braided tubular member 100, the radially outward wire segments 308 may cover or go over the radially inward wire segments 310 and the radially inward wire segments 310 may be uncoated and devoid of the coating 314 and/or the radially outward wire segments 308 may extend radially outward of the radially inward wire segments 310 such that the coating 314 only covers portions of the radially outward wire segments 308, while not contacting the radially inward wire segments 308, thus leaving the radially inward wire segments 308 uncoated or devoid of the coating 314. Furthermore, because the braided tubular member 100 is in the axially elongated state when the coating 314 is applied, the uncoated length (i.e., $X_2$) of the radially inward wire segments 310 may be greater than the uncoated length (i.e., $X_1$) of the radially inward wire segments 310, if the coating 314 was applied when the braided tubular member 100 was in the nominally deployed state. In some instances, the coating 314 may extend around less than the entire circumference of the radially outward wire segments 308 at the crossover points 122. For, example, the coating 314 may only partially extend around the circumference of the radially outward wire segments 308, leaving the portion of the radially outward wire segments 308 facing and/or in contact with the radially inward wire segments 310 devoid of the coating 314.

Figure 4A:
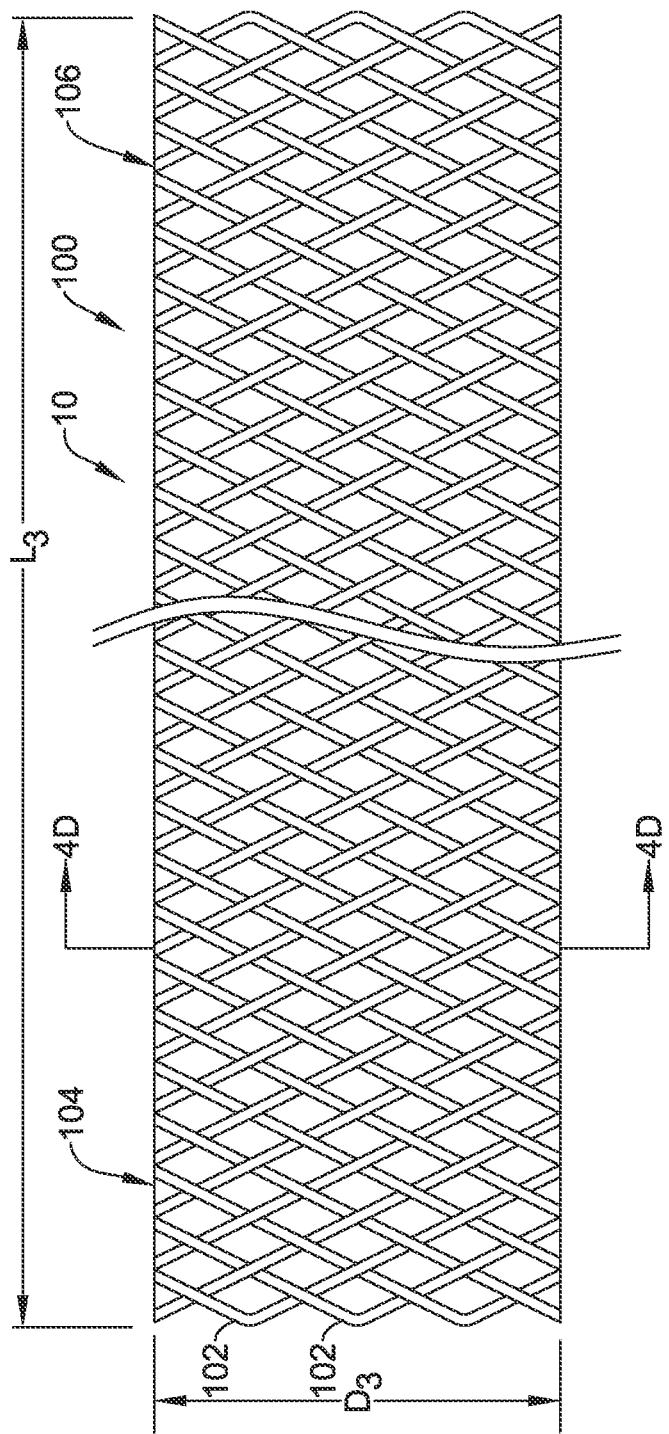
FIG. 4A depicts the exemplary stent of FIG. 1A in an axially contracted state.

FIG. 4A depicts the exemplary braided tubular member 100 of the stent in an axially contracted state (or radially expanded state). In some cases, the braided tubular member 100 may have been adjusted into the axially contracted state using an applied force that axially moves the first 104 and second 106 ends together. The applied force moves the braided tubular member 100 from its nominally deployed state (i.e., equilibrium state without externally applied forces) to the axially contracted state. As shown, the braided tubular member 100 has been radially expanded and the diameter of the braided tubular member 100 has increased from diameter $D_1$ at the nominally deployed state to diameter $D_3$ at the axially contracted state, and the length of the braided tubular member 100 has decreased from length $L_1$ at the nominally deployed state to $L_3$ at the axially contracted state.

Figure 4B:
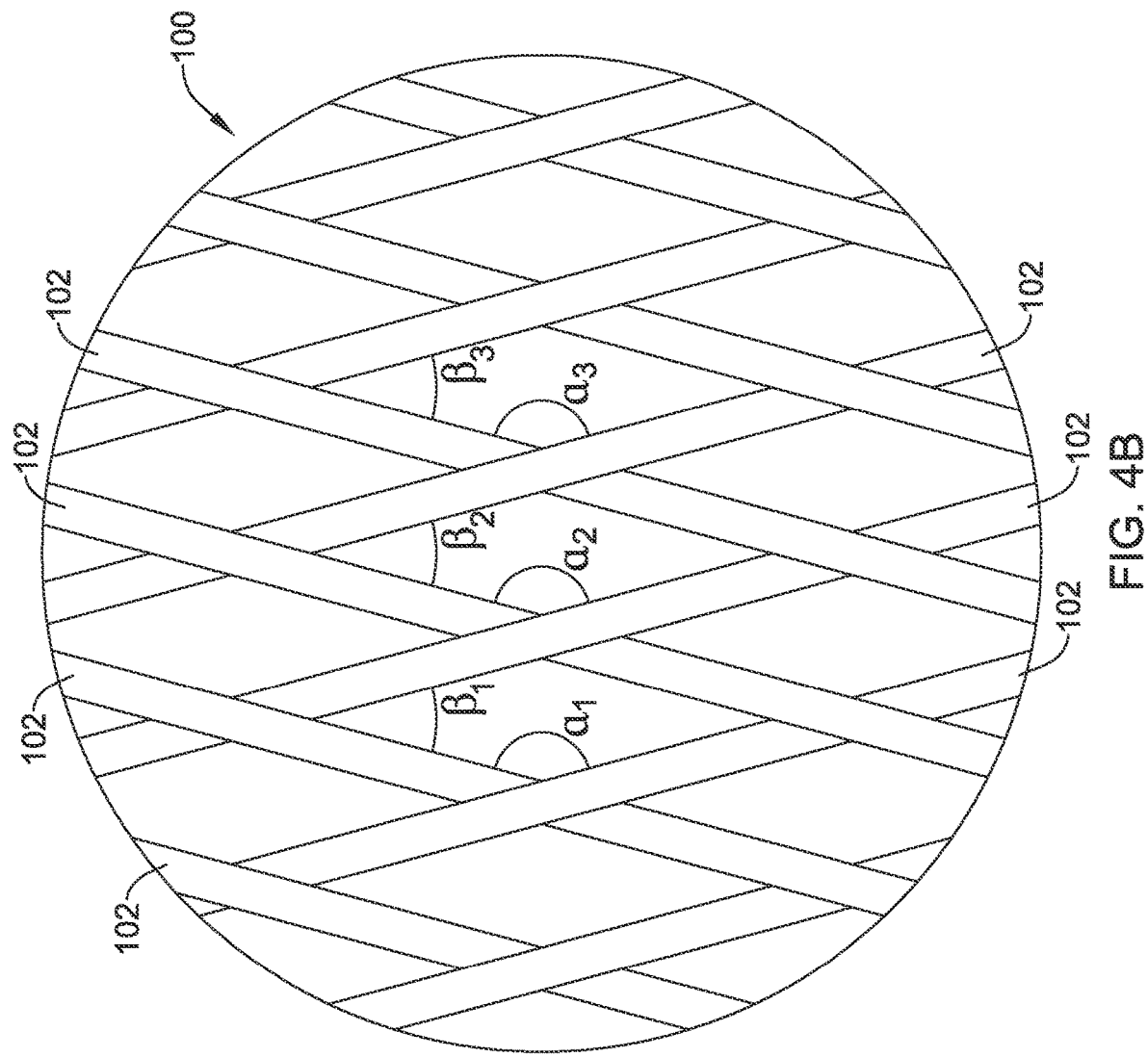
FIG. 4B depicts an enlarged view of the braided tubular member of the stent of FIG. 1A in an axially contracted state.

FIG. 4B depicts an enlarged view of a portion of the braided tubular member 100 in the axially contracted state as described in FIG. 4A. As shown, the pivot angles $\alpha_1$-$\alpha_3$ have increased from their nominally deployed measured values in FIG. 3B to their axially contracted state measured values in FIG. 4B. Also, the pivot angles $\beta_1$-$\beta_3$ have decreased from their nominally deployed measured values in FIG. 3B to their axially contracted state measured values in FIG. 4B.

FIG. 4C is an enlarged view of a crossover point of intersecting wires of the braided tubular member 100 illustrating movement of the intersecting wires between the nominally deployed state (dashed lines) and an axially contracted state (solid lines). The view 304 (dashed lines) depicts the braided tubular member 100 in the nominally deployed state and the view 406 (solid lines) depicts the braided tubular member 100 in the axially contracted state. As shown, the view 304 is superimposed (illustrated using dashed lines) onto the view 406 with a common pivot point at the crossover point 322 of a radially outward wire segment 308 of a wire 102 and a radially inward wire segment 310 of a wire 102. Moreover, FIG. 4C is used to illustrate one radially outward wire segment 308 and one radially inward wire segment 310. In the nominally deployed state shown in view 304, the radially outward wire segment 308 covers, goes over, is above, and/or is radially outward of and contacts a length $X_1$ of the radially inward wire segment 310. However, in the axially contracted state shown in view 406 the radially outward wire segment 308 cover, goes over, is above, and/or is radially outward of and contacts a length $X_3$ of the radially inward wire segment 310. As can be seen, the length of $X_3$ of the radially inward wire segment 310 in contact with the radially outward wire segment 308 in the axially contracted state may be greater than the length $X_1$ of the radially inward wire segment 310 in contact with the radially outward wire segment 308 in the nominally deployed state. As described in further detail below, the uncoated portions of the wires (e.g., sections of each wire that are not coated, and thus devoid of a coating) may have a length greater than or equal to the length $X_3$ that the radially inward wire segment 310 is in contact with the radially outward wire segment 308 in the axially contracted state to ensure the outward wire segment 308 does not contact or rub across the coating on the coated portion of the wire forming the inward wire segment 310 on either side of the crossover point.

FIG. 4D depicts a cross-sectional view of the braided tubular member 100 in the axially contracted state taken along line 4D-4D of FIG. 4A. As discussed above, the radially outward wire segment 308 may reside radially outward of the radially inward wire segment 310 at each crossover point. As shown in FIG. 4D, select portions of the braided tubular member 100 may be coated with a coating applied directly thereto. For example, the radially outward wire segments 308 may be coated with the coating 314 using such techniques as roll coating, dot matrix print coating, and spray coating, for example, while leaving an uncoated length of the inward wire segments 310 at each crossover point. In certain embodiments, when the coating 314 is applied to the braided tubular member 100, the radially outward wire segments 308 may cover or go over the radially inward wire segments 310 and the radially inward wire segments 310 may be uncoated and devoid of the coating 314 and/or the radially outward wire segments 308 may extend radially outward of the radially inward wire segments 310 such that the coating 314 only covers portions of the radially outward wire segments 308, while not contacting the radially inward wire segments 308, thus leaving the radially inward wire segments 308 uncoated or devoid of the coating 314. Furthermore, because the braided tubular member 100 is in the axially contracted state when the coating 314 is applied, the uncoated length (i.e., $X_3$) of the radially inward wire segments 310 may be greater than the uncoated length (i.e., $X_1$) of the radially inward wire segments 310, if the coating 314 was applied when the braided tubular member 100 was in the nominally deployed state. In some instances, the coating 314 may extend around less than the entire circumference of the radially outward wire segments 308 at the crossover points 122. For, example, the coating 314 may only partially extend around the circumference of the radially outward wire segments 308, leaving the portion of the radially outward wire segments 308 facing and/or in contact with the radially inward wire segments 310 devoid of the coating 314.

Figure 5:
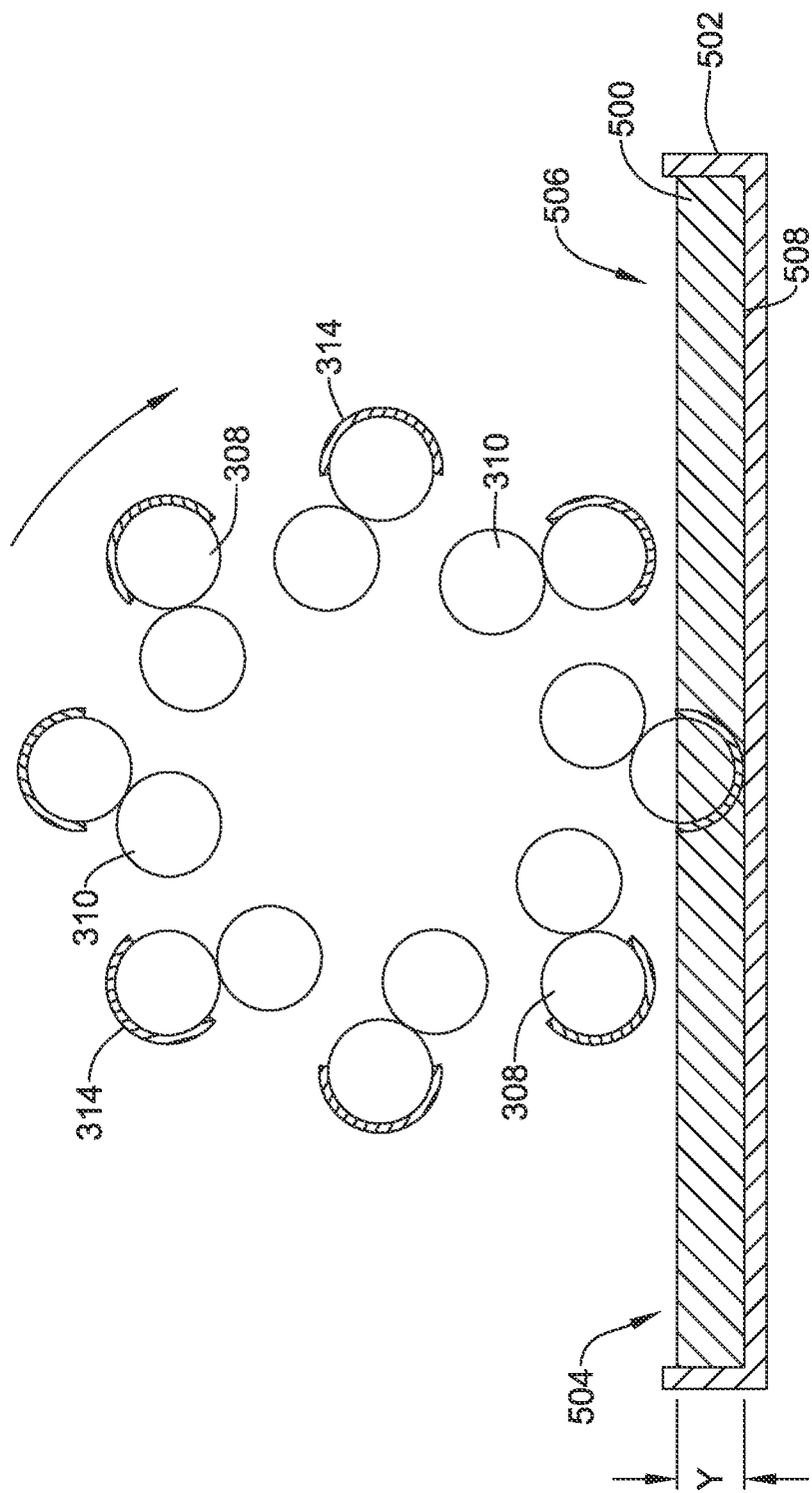
FIG. 5 depicts an exemplary application of a coating to the stent of FIG. 1A using a roll coating technique.

FIG. 5 depicts an exemplary application of a coating material 500 to form the coating 314 on the braided tubular member 100 using a roll coating technique. According to various embodiments, the braided tubular member 100 may be in either the axially elongated state or the axially contracted state while the coating material 500 is applied to the braided tubular member. Automated placement equipment (not shown) may be used to place the braided tubular member 100 into a basin 502 that contains the coating material 500. In this embodiment, the braided tubular member 100 may be placed into the basin 502 near a first end 504 of the basin and advanced toward a second end 506 of the basin 502. As the braided tubular member 100 is advanced through the basin 502, the braided tubular member 100 may roll about its longitudinal axis (e.g., longitudinal axis 204, from FIG. 2). In some cases, the rolling may be due to a frictional force between a bottom 508 of the basin 502 and the radially outward wire segments (e.g., the radially outward wire segments 308). For instance, the radially outward wire segments may come into contact with the bottom 508 and the frictional force may push the radially outward wire segments in the opposite direction that the braided tubular member 100 is being advanced. In response, the braided tubular member 100 may rotate and additional radially outward wire segments may be placed into the coating 500, come into contact with the bottom 508 of the basin 502, and continue the rotation of the braided tubular member 100 until the abluminal surface of the braided tubular member 100 is coated with the coating material 500, as desired, to form the coating 314. In another example, the automated placement equipment may rotate the braided tubular member 100 on its own through the coating material 500 with or without advancing the braided tubular member 100 through the basin 502. Regardless of the method of rotation, according to various embodiments, because the braided tubular member 100 is in the axially elongated state or the axially contracted state during the application of the coating material 500 to form coating 314 on the braided tubular member 100, the radially outward wire segments (e.g., radially outward wire segments 308) may be radially outward of the radially inward wire segments (e.g., radially inward wire segments 310). In addition, braided tubular member 100 may be submerged in the coating material 500 in the basin 502 to a depth (i.e., Y) that is less than the diameter d of the radially outward wire segments 308. Because the radially inward wire segments 310 are positioned radially inward of the radially outward wire segments 308 and the submerged depth Y into the coating material 500 is less than the diameter d of the wires of the radially outward wire segments 308, the coating material 500 may be applied to a surface of the radially outward wire segments 308 without contacting the coating material 500 to a surface of the radially inward wire segments 310 (i.e., the radially inward wire segments 310 avoid entering or being submerged into the coating material 500. As such, the radially inward wire segments 310 may remain uncoated and devoid of the coating material 500 during the coating process for applying the coating 314 to the radially outward wire segments 308. Furthermore, because the braided tubular member 100 is in either the axially elongated or axially contracted state when the braided tubular member 100 is rolled through the coating material 500, or otherwise subjected to a coating process, the uncoated length of the radially inward wire segments 310 of the wires 102 may be greater than the length of the radially inward wire segments 310 contacting the radially outward wire segments 308 at the crossover points 322 when in the nominally deployed length.

The coating 314 may be any suitable biologically acceptable coating. In some instances, the coating 314 may include a therapeutic agent such as a non-genetic therapeutic agent, a biomolecule, a small molecule, or cells.

Exemplary non-genetic therapeutic agents include anti-thrombogenic agents such as heparin, heparin derivatives, prostaglandin (including micellar prostaglandin E1), urokinase, and PPack (dextrophenylalanine proline arginine chloromethyl ketone); anti-proliferative agents such as enoxaparin, angiopeptin, sirolimus (rapamycin), tacrolimus, everolimus, zotarolimus, biolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estradiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc-oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis(2-aminoethyl) ethyleneglycol-N,N,N',N'-tetraacetic acid and mixtures thereof; antibiotics such as gentamicin, rifampin, minocycline, and ciprofloxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds including anti-thrombin antibodies, platelet receptor antagonists, anti-platelet receptor antibodies, enoxaparin, hirudin, warfarin sodium, dicumarol, aspirin, prostaglandin inhibitors, platelet aggregation inhibitors such as cilostazol and tick antiplatelet factors; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms; inhibitors of heat shock proteins such as geldanamycin; angiotensin converting enzyme (ACE) inhibitors; beta-blockers; βAR kinase (βSARK) inhibitors; phospholamban inhibitors; protein-bound particle drugs such as ABRAXANE™; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include SERCA 2 protein, monocyte chemoattractant proteins ("MCP-1") and bone morphogenic proteins ("BMPs"), such as, for example, BMP-2, BMP-3, BMP-4, BMP-5, BMP-6 (VGR-1), BMP-7 (OP-1), BMP-8, BMP-9, BMP-10, BMP-11, BMP-12, BMP-13, BMP-14, BMP-15. Preferred BMPs are any of BMP-2, BMP-3, BMP-4, BMP-5, BMP-6, and BMP-7.

These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNAs encoding them. Non-limiting examples of genes include survival genes that protect against cell death, such as anti-apoptotic Bcl-2 family factors and Akt kinase; serca 2 gene; and combinations thereof. Non-limiting examples of angiogenic factors include acidic and basic fibroblast growth factors, vascular endothelial growth factor, epidermal growth factor, transforming growth factors α and β, platelet-derived endothelial growth factor, platelet-derived growth factor, tumor necrosis factor α, hepatocyte growth factor, and insulin-like growth factor. A non-limiting example of a cell cycle inhibitor is a cathepsin D (CD) inhibitor. Non-limiting examples of anti-restenosis agents include p15, p16, p18, p19, p21, p2'7, p53, p5'7, Rb, nFkB and E2F decoys, thymidine kinase and combinations thereof and other agents useful for interfering with cell proliferation.

Exemplary small molecules include hormones, nucleotides, amino acids, sugars, and lipids and compounds that have a molecular weight of less than 100 kD.

Exemplary cells include stem cells, progenitor cells, endothelial cells, adult cardiomyocytes, and smooth muscle cells. Cells can be of human origin (autologous or allogeneic) or from an animal source (xenogeneic), or genetically engineered. Non-limiting examples of cells include side population (SP) cells, lineage negative (Lin$^-$) cells including Lin$^-$CD34$^-$, Lin$^-$CD34$^+$, Lin$^-$c Kit$^+$, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, G$_0$ cells, endothelial cells, adult cardiomyocytes, fibroblasts, smooth muscle cells, adult cardiac fibroblasts +5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

Any of the therapeutic agents may be combined to the extent such combination is biologically compatible.

In some instances, the coating 314 may be a polymeric coating including any of the above mentioned therapeutic agents may be incorporated into the polymeric coating on selected portions of the braided tubular member 100. The polymers of the polymeric coatings may be biodegradable or non-biodegradable. Non-limiting examples of suitable non-biodegradable polymers include polystyrene; polystyrene maleic anhydride; polyisobutylene copolymers such as styrene-isobutylene-styrene block copolymers (SIBS) and styrene-ethylene/butylene-styrene (SEBS) block copolymers; polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides including poly(methylmethacrylate-butylacetate-methylmethacrylate) block copolymers; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHYDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L-lactide), poly (lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butyl acrylate; polyhydroxybutyrate valerate and blends; polycarbonates such as tyrosine-derived polycarbonates and acrylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropyl methyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc calcium phosphate.

Such coatings may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent/therapeutic agent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

Figure 6A:
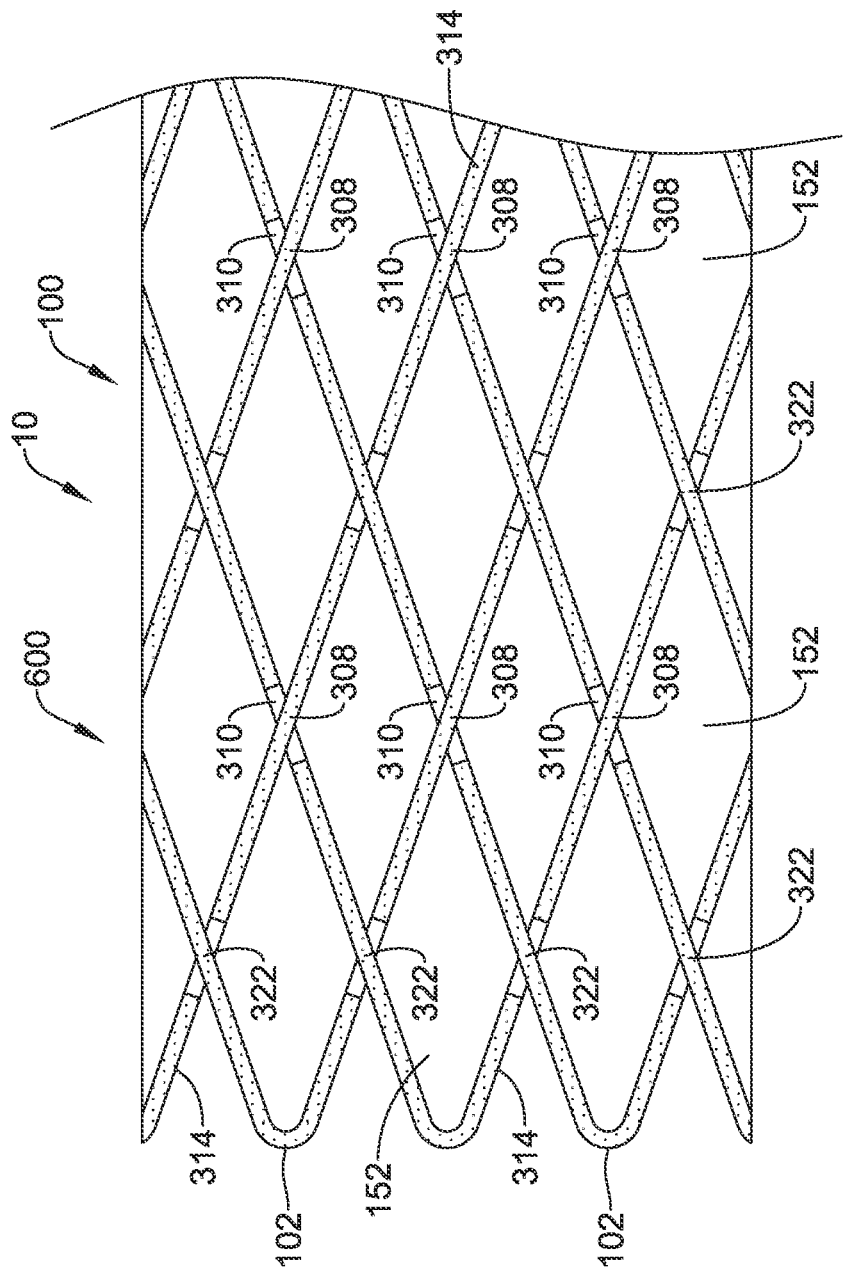

FIG. 6A depicts an exemplary section 600 of the braided tubular member 100 in the axially elongated state after application of the coating 314, as discussed above. As shown, radially outward facing exposed surfaces of portions of the braided wires 102 have been coated with the coating 314. However, other portions of the braided wires 102 and the open cells 152 are left uncoated. The uncoated portions include the radially inward wire segments 310 of the wires 102 located at the crossover points 322. Moreover, as discussed above, the uncoated length of the radially inward wire segments 310 may be greater than the diameter of the wire 102 of the radially outward wire segment 308 at the crossover points 322. In some cases, the uncoated length of the uncoated radially inward wire segments 310 may enable radially outward wire segments 308 to pivot relative to the radially inward wire segments 310 at the crossover points 322 as the braided tubular member 100 is compressed and elongated back and forth between the axially elongated state, the nominally deployed state, and the axially contracted state without the radially outward wire segments 308 contacting the coating 314 on the coated portions of the braided wires 102. In other words, the radially outward wire segments 308 may not be hindered by the coating 314 and may have an uninhibited range of motion as they pivot at the crossover points 322 back and forth between the axially elongated state, the nominally deployed state, and the axially contracted state. As such, the coating 314 may not be damaged as the radially outward wire segments 308 pivot relative to the radially inward wire segments 310 at the crossover points 322 when moving between the axially elongated state, the nominally deployed state, and the axially contracted state.

FIG. 6B depicts the exemplary section 600 of the braided tubular member 100 in the axially contracted state after application of the coating 314, as discussed above. As described in regard to FIG. 6A, because the coating 314 was applied while the braided tubular member 100 was either in the axially elongated state or the axially contracted state, the length of the uncoated radially inward wire segments 310 may allow the radially outward wire segments 308 to pivot at the crossover points 322 without contacting the coating 314 on the coated portions of the braided wires 102. As a result, the range of pivoting motion of the radially outward wire segments 308 at the crossover points 322 may be uninhibited at the crossover points 322 as the radially outward wire segments 308 pivot relative to the radially inward wire segments 310 at the crossover points 322 when moving between the axially elongated state, the nominally deployed state, and the axially contracted state.

Figure 6C:
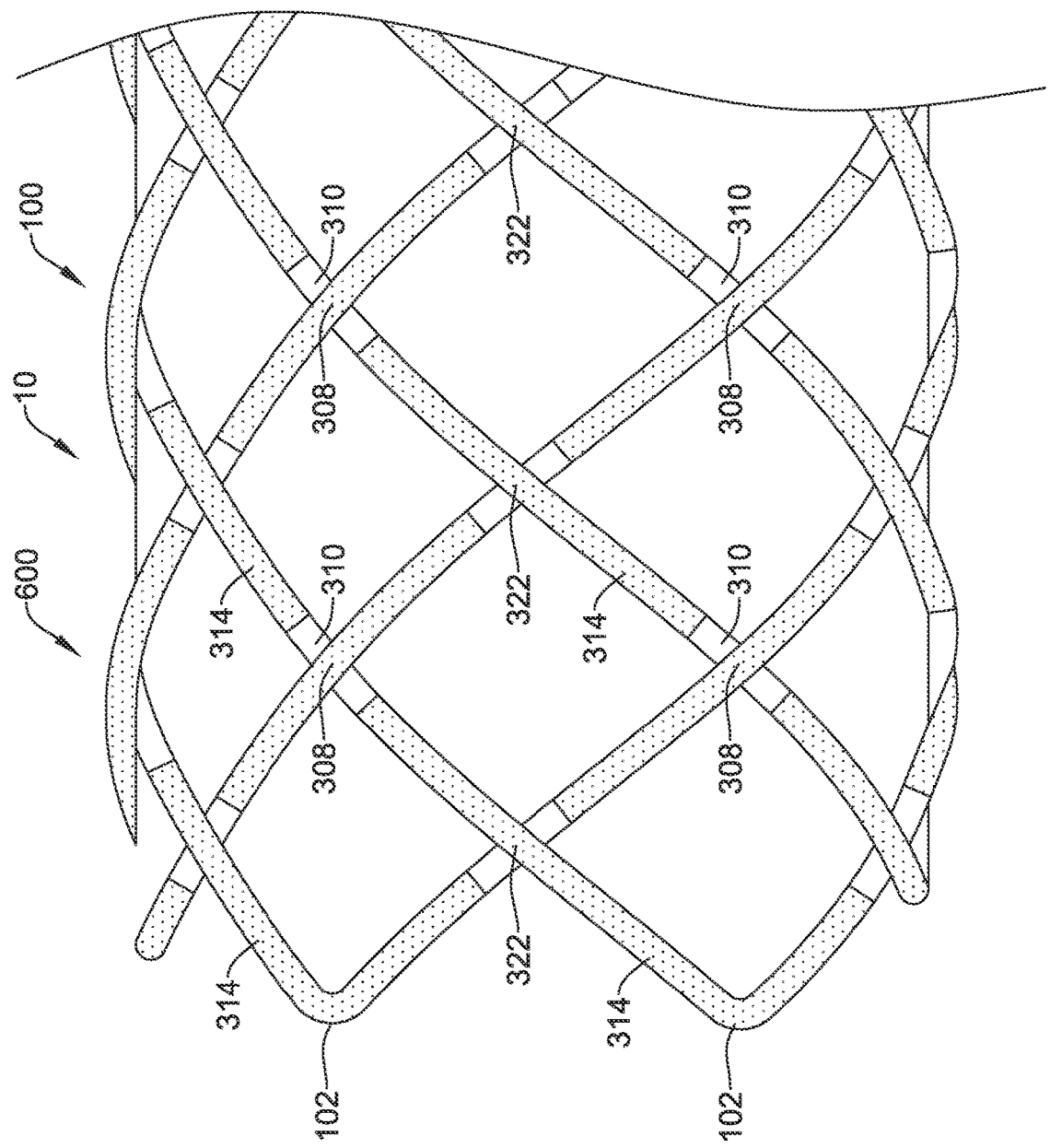

FIG. 6C depicts the exemplary section 600 of the braided tubular member 100 in the nominally deployed state after application of the coating 314 using the roll coating technique, discussed above. As described in regard to FIGS. 6A-6B, because the coating 314 was applied while the braided tubular member 100 was either in the axially elongated state or the axially contracted state, the length of the uncoated radially inward wire segments 310 may allow the radially outward wire segments 308 to pivot at the crossover points 322 without contacting the coating 314 on the coated portions of the intersecting braided wires 102 at the crossover points 322. As a result of the coating process, each of the plurality of braided wires 102 includes radially outward wire segments 308 including the coating 312 alternating with a plurality of radially inward wire segments 310 devoid of the coating along a length of the wire 102. The length of each of the uncoated radially inward wire segments 310 may be different than or the same as the length of each of the coated radially outward wire segments 308 along each wire 102. For example, the length of each of the uncoated radially inward wire segments 310 may be less than the length of each of the coated radially outward wire segments 308 along each wire 102.

Figure 7A:
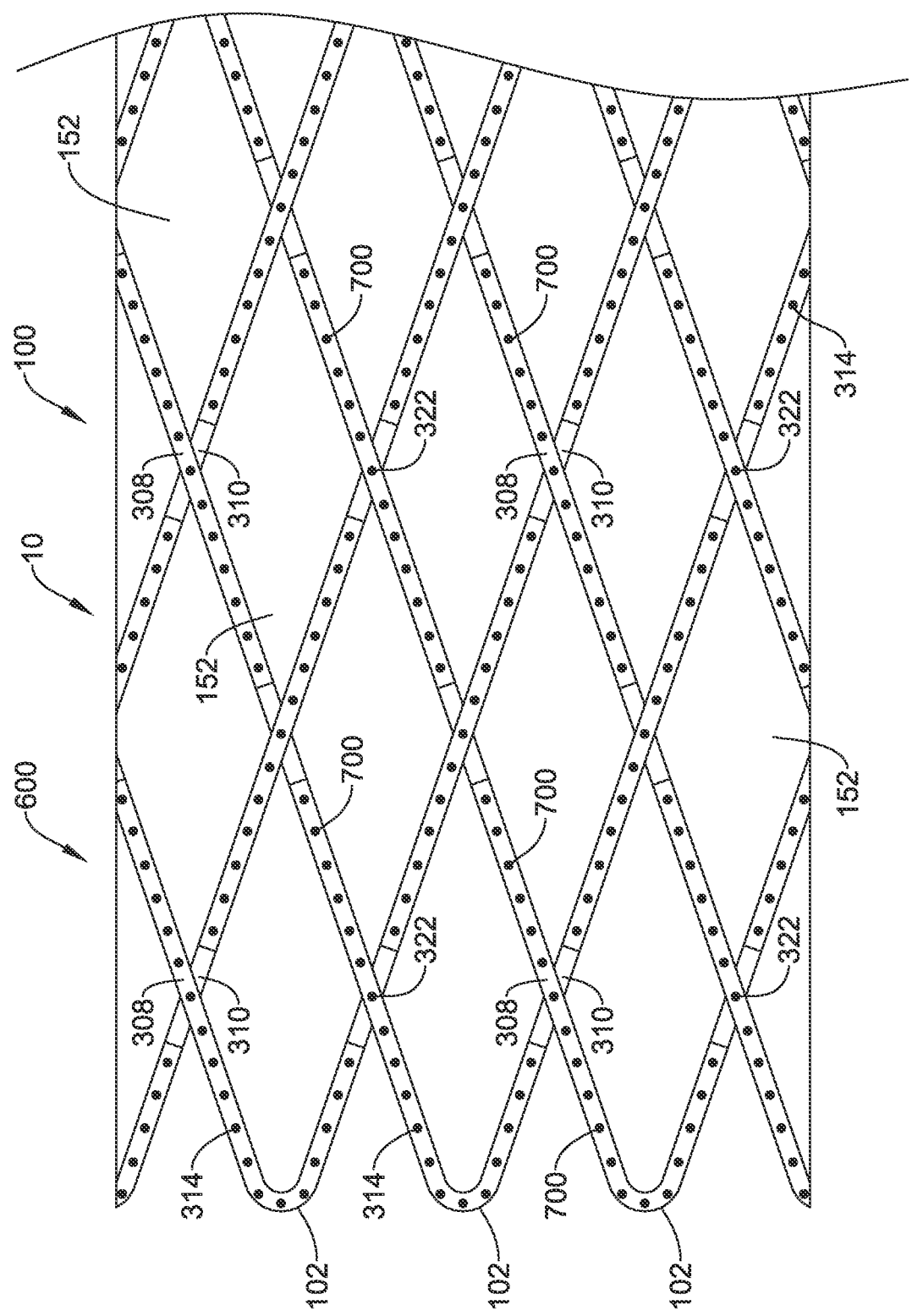
FIGS. 7A-7C depict the braided tubular member of the stent in various states after application of the coating using an alternative coating process.

FIG. 7A depicts the exemplary section 600 of the braided tubular member 100 in the axially elongated state after application of the coating 314 using a dot matrix coating technique. In a dot matrix coating technique, an array of coating elements may be selectively turned on and off by a controller. The number and location of the coating elements may be described as a matrix having M possible positions on the rows and N possible positions on the columns (which together can be thought of as a cell). In some cases, the coating elements may apply individual coating dots 700 to form the coating 314 on select portions of the braided tubular member 100 by a technique in which the coating 314 is propelled toward the braided tubular member 100 in discrete locations. The individual coating dots 700 are illustrated as being spaced away from one another, herein it is contemplated that each coating dot 700 may contact or overlap with each successive coating dot 700 along the coated portion of the wires 102 to form the coating 314. In some cases, the coating 314 may be transferred from a ribbon saturated with the coating 314 to the braided tubular member 100 by impacting an element such as a wire against the coated ribbon to transfer the coating 314 from the coated ribbon to the braided tubular member 100. These are just a couple of dot matrix coating techniques. Exemplary dot matrix coating techniques are described in European Patent No. EP 2 045 019 B1, entitled Method and Apparatus for Coating a Stent, the contents of which are incorporated herein by reference. In other cases, another dot matrix coating technique known in the art may be used.

As shown in FIG. 7A, coating dots 700 have been disposed on radially outward facing exposed surfaces of portions of the braided wires 102. However, other portions of the braided wires 102 and the open cells 152 are left uncoated. The uncoated portions include the radially inward wire segments 310 of the wires 102 that were covered by the radially outward wire segments 308 during application of the coating dots 700. Moreover, as discussed above, the length of the uncoated portions of the wires 102 defining the radially inward wire segments 310 may be greater than the diameter of the wire 102 of the radially outward wire segment 308 at the crossover points 322. In some cases, the uncoated length of the uncoated radially inward wire segments 310 may enable radially outward wire segments 308 to pivot relative to the radially inward wire segments 310 at the crossover points 322 as the braided tubular member 100 is compressed and elongated back and forth between the axially elongated state, the nominally deployed state, and the axially contracted state without the radially outward wire segments 308 contacting the coating 314 on the coated portions of the braided wires 102. In other words, the radially outward wire segments 308 may not be hindered by the coating 314 and may have an uninhibited range of motion as they pivot at the crossover points 322 back and forth between the axially elongated state, the nominally deployed state, and the axially contracted state. As such, the coating 314 may not be damaged as the radially outward wire segments 308 pivot relative to the radially inward wire segments 310 at the crossover points 322 when moving between the axially elongated state, the nominally deployed state, and the axially contracted state.

Figure 7B:
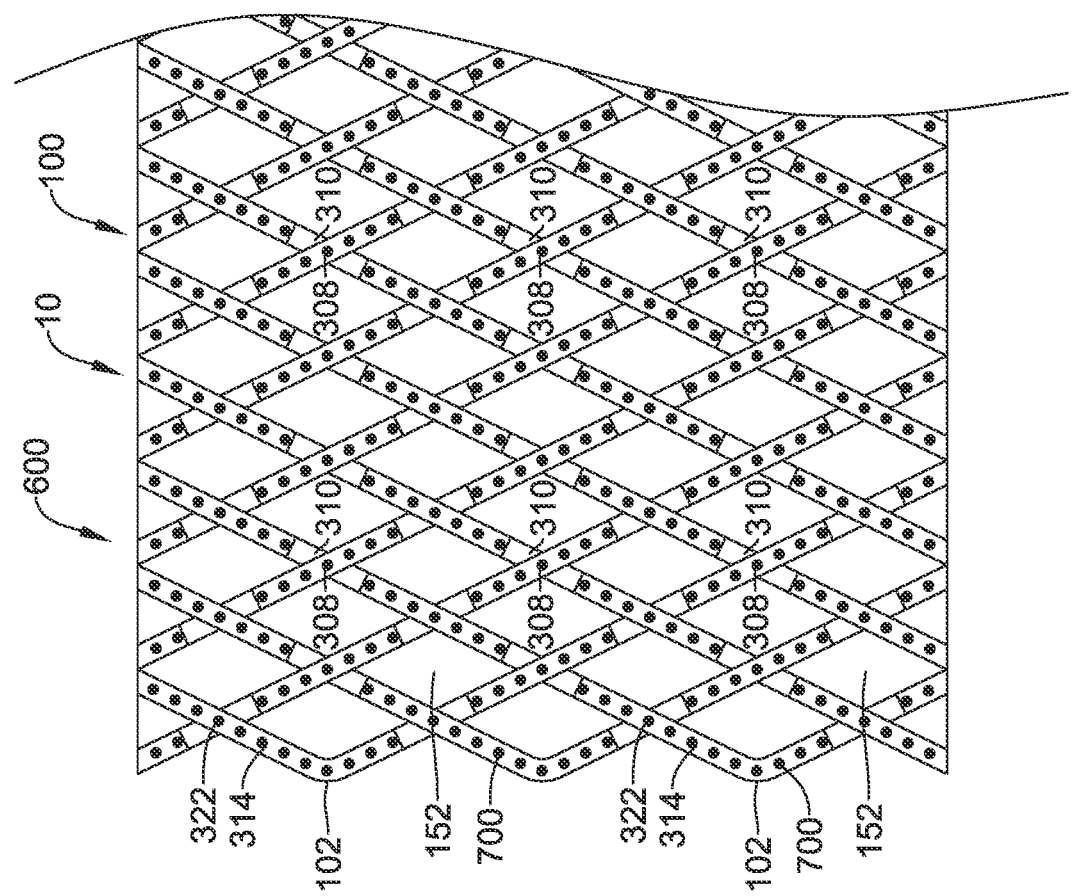

FIG. 7B depicts the exemplary section 600 of the braided tubular member 100 in the axially contracted state after application of the coating 314 using the dot matrix coating technique, discussed above. As described in regard to FIG. 7A, because the coating dots 700 forming the coating 314 were applied while the braided tubular member 100 was either in the axially elongated state or the axially contracted state, the length of the uncoated radially inward wire segments 310 may allow the radially outward wire segments 308 to pivot at the crossover points 322 without contacting the coating 314 on the coated portions of the braided wires 102. As a result, the range of pivoting motion of the radially outward wire segments 308 at the crossover points 322 may be uninhibited at the crossover points 322 as the radially outward wire segments 308 pivot relative to the radially inward wire segments 310 at the crossover points 322 when moving between the axially elongated state, the nominally deployed state, and the axially contracted state.

Figure 7C:
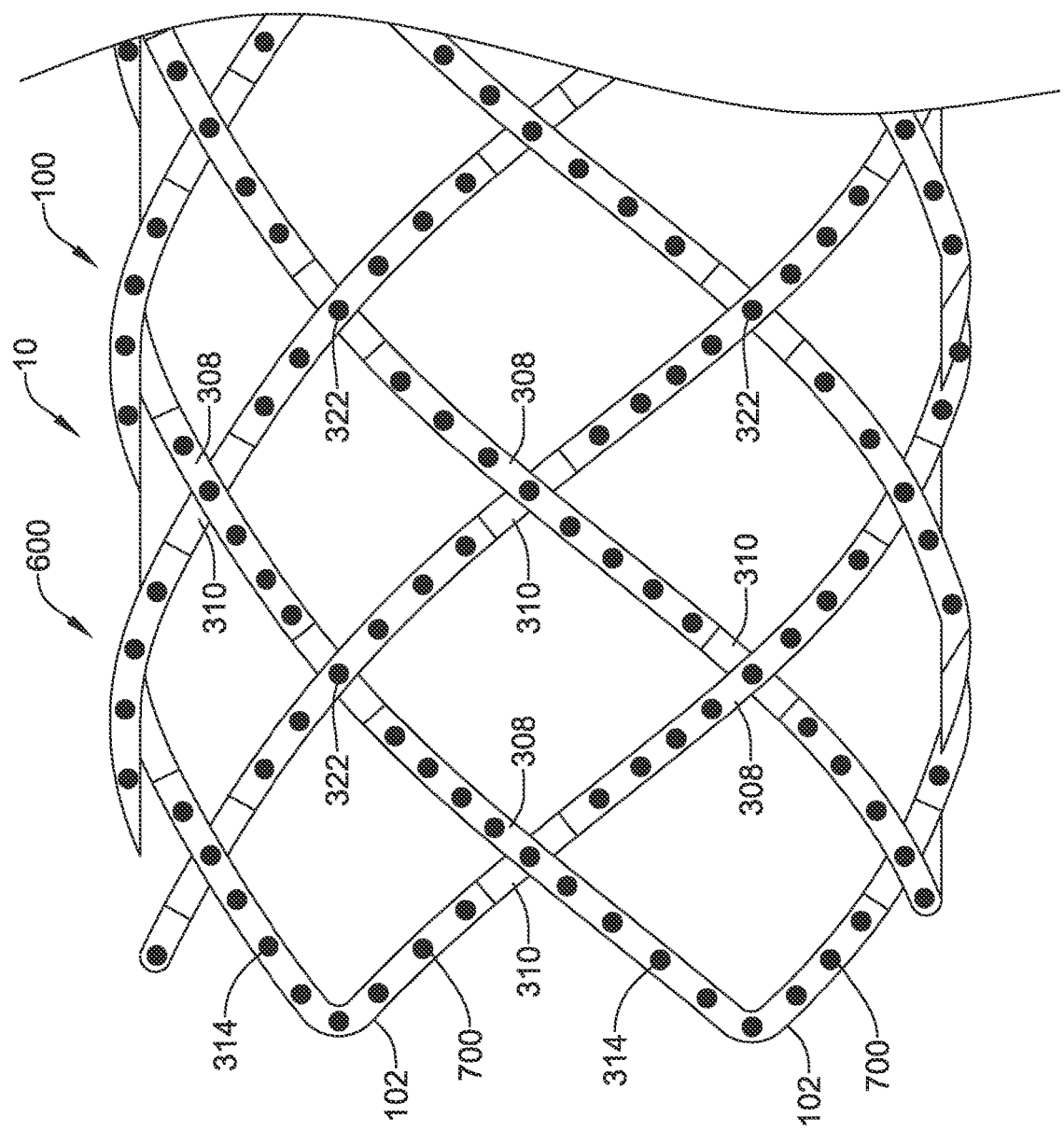

FIG. 7C depicts the exemplary section 600 of the braided tubular member 100 in the nominally deployed state after application of the coating 314 using the dot matrix coating technique, discussed above. As described in regard to FIGS. 7A-7B, because the coating dots 700 forming the coating 314 were applied while the braided braided tubular member 100 was either in the axially elongated state or the axially contracted state, the length of the uncoated radially inward wire segments 310 may allow the radially outward wire segments 308 to pivot at the crossover points 322 without contacting the coating 314 on the coated portions of the intersecting braided wires 102 at the crossover points 322. As a result of the coating process, each of the plurality of braided wires 102 includes radially outward wire segments 308 including the coating 312 alternating with a plurality of radially inward wire segments 310 devoid of the coating along a length of the wire 102. The length of each of the uncoated radially inward wire segments 310 may be different than or the same as the length of each of the coated radially outward wire segments 308 along each wire 102. For example, the length of each of the uncoated radially inward wire segments 310 may be less than the length of each of the coated radially outward wire segments 308 along each wire 102.

The roll coating technique and the dot matrix technique are just a couple of coating techniques that may be used to apply a coating to a braided tubular member (e.g., braided tubular member 100) in an axially elongated state or an axially contracted state that results in radially outward wire segments 308 including the coating 312 intersecting radially inward wire segments 310 devoid of the coating at crossover points 322 along a length and around a circumference of a braided tubular member 100. Thus, the coated stent 10, may be formed of a plurality of interbraided wires 102, wherein each of the interbraided wires 102 includes radially outward wire segments 308 including the coating 312 alternating with a plurality of radially inward wire segments 310 devoid of the coating along a length of the wire 102. In some cases, other techniques or a combination of coating techniques known in the art may be used.

Figure 8A:
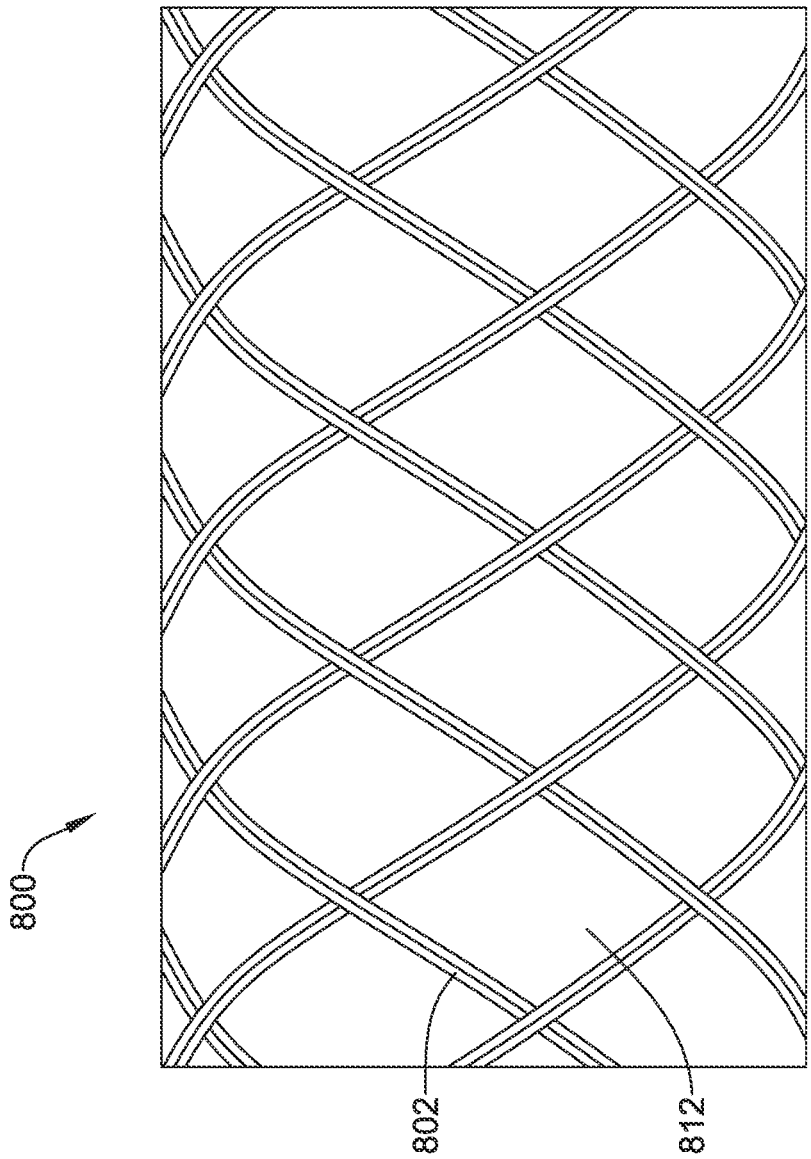
FIGS. 8A-8D depict alternative braid patterns of exemplary stents.

FIGS. 8A-8D depict exemplary braid patterns of stents that may have braided tubular members configured for application of a coating, as described herein. The stents depicted in FIGS. 8A-8D are illustrated in a nominally deployed state. In FIG. 8A, a braided tubular member 800 is shown having a braid pattern with pairs of wires 802 intersecting to define open cells 812 therebetween. The braided tubular member 800 is relatively symmetric and the axial displacement of wired pairs 802 is relatively symmetric. As discussed above, the wired pairs 802 may be the same or may be different (e.g., may be made of different materials).

Figure 8B:
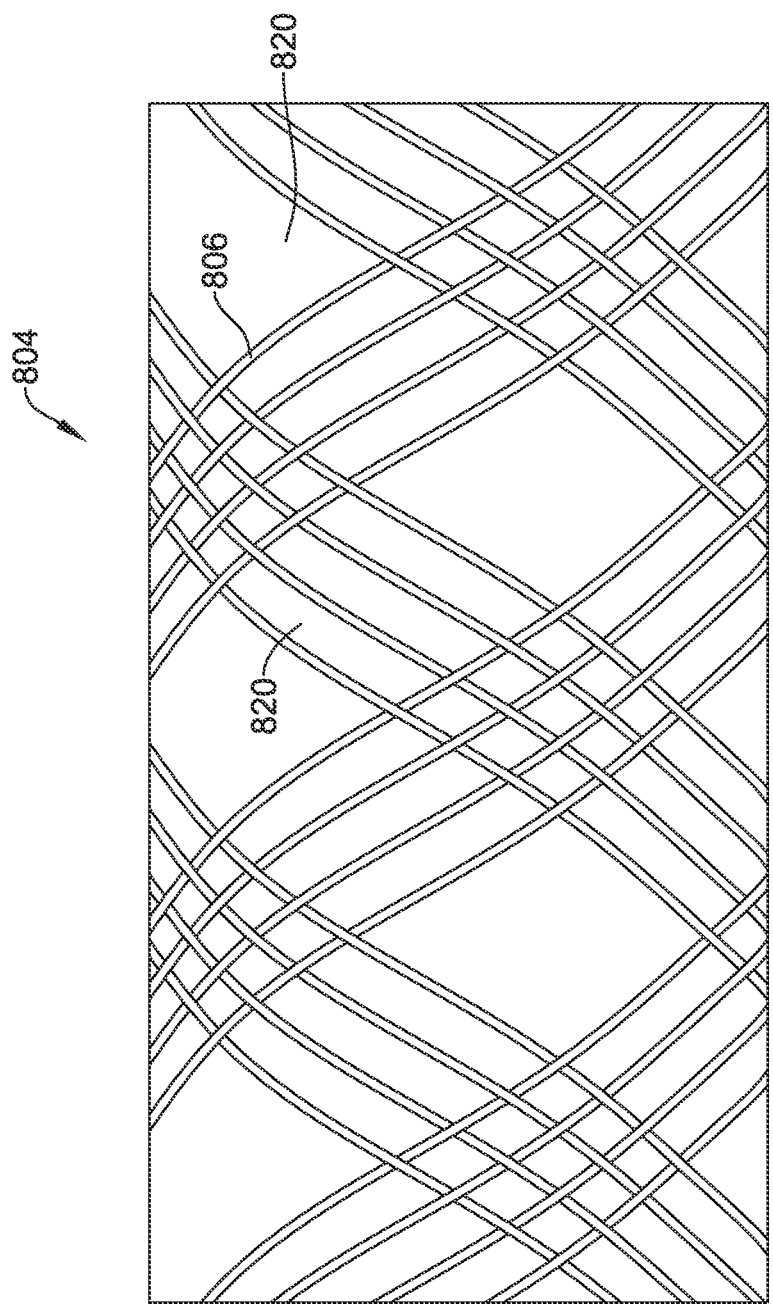

Turning to FIG. 8B, a braided tubular member 804 is shown having a braid pattern with open cells 820 defined between intersecting wires 806. Braided wires 806 are also axial displaced relatively asymmetrically, thus providing open cells 820 of multiple sizes. The braided wires 806 may be the same or may be different (e.g., may have the same or different dimensions, shapes and/or materials of construction).

Figure 8C:
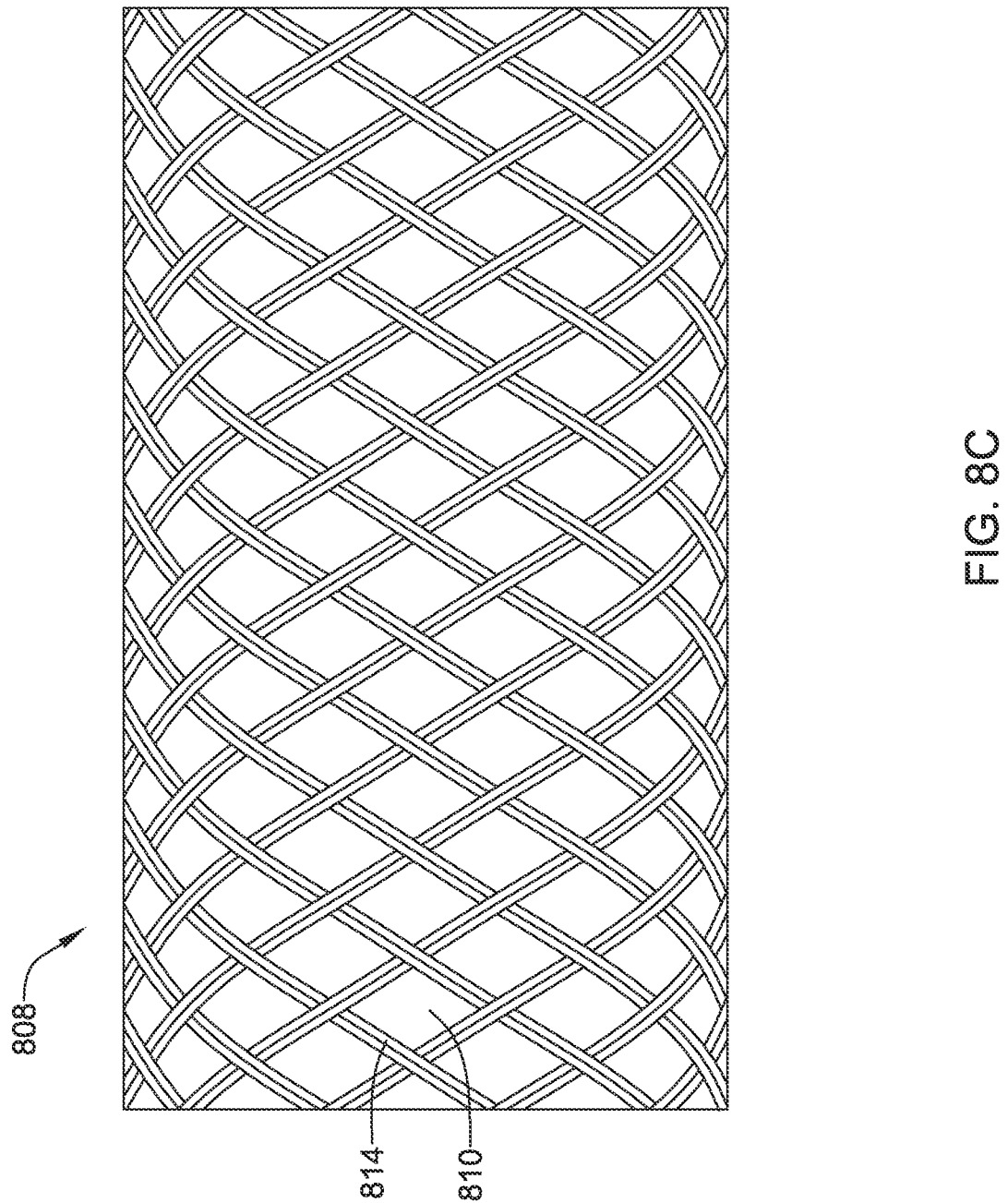

Turning to FIG. 8C, a braided tubular member 808 is shown having another braid pattern. The braided tubular member 808 may be configured similar to the braided tubular member 800 (from FIG. 8A), however, open cells 810 may have a smaller area than open cells 812 (shown in FIG. 8A). This may occur because wired pairs 814 are more tightly wound than wired pairs 802.

Figure 8D:
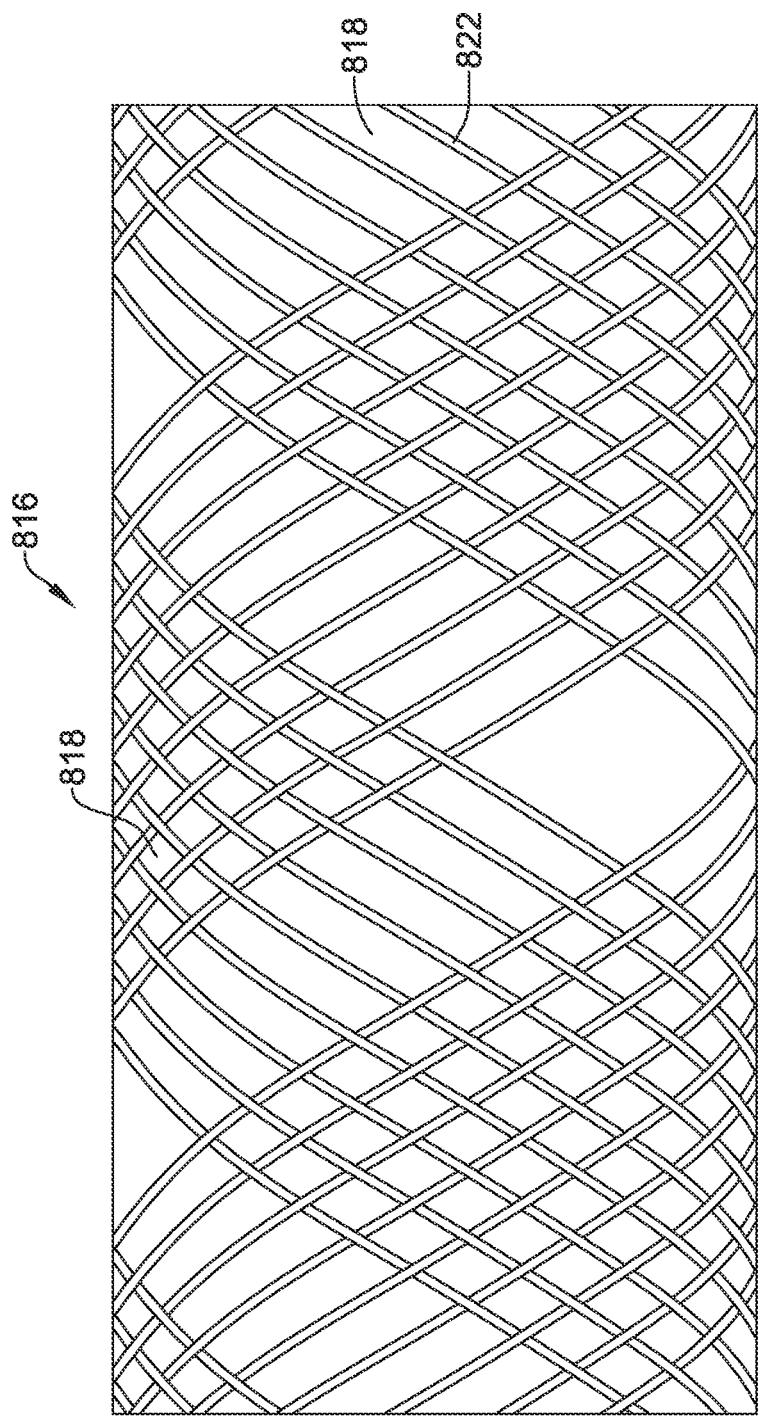

Turning to FIG. 8D, a braided tubular member 816 is shown having another braid pattern. The braided tubular member 816 may be configured similar to the braided tubular member 804 (from FIG. 8B), however, open cells 818 may have a smaller area than open cells 820 (shown in FIG. 8B). This may occur because braided wires 822 are more tightly wound than braided wires 806.

Figure 9:
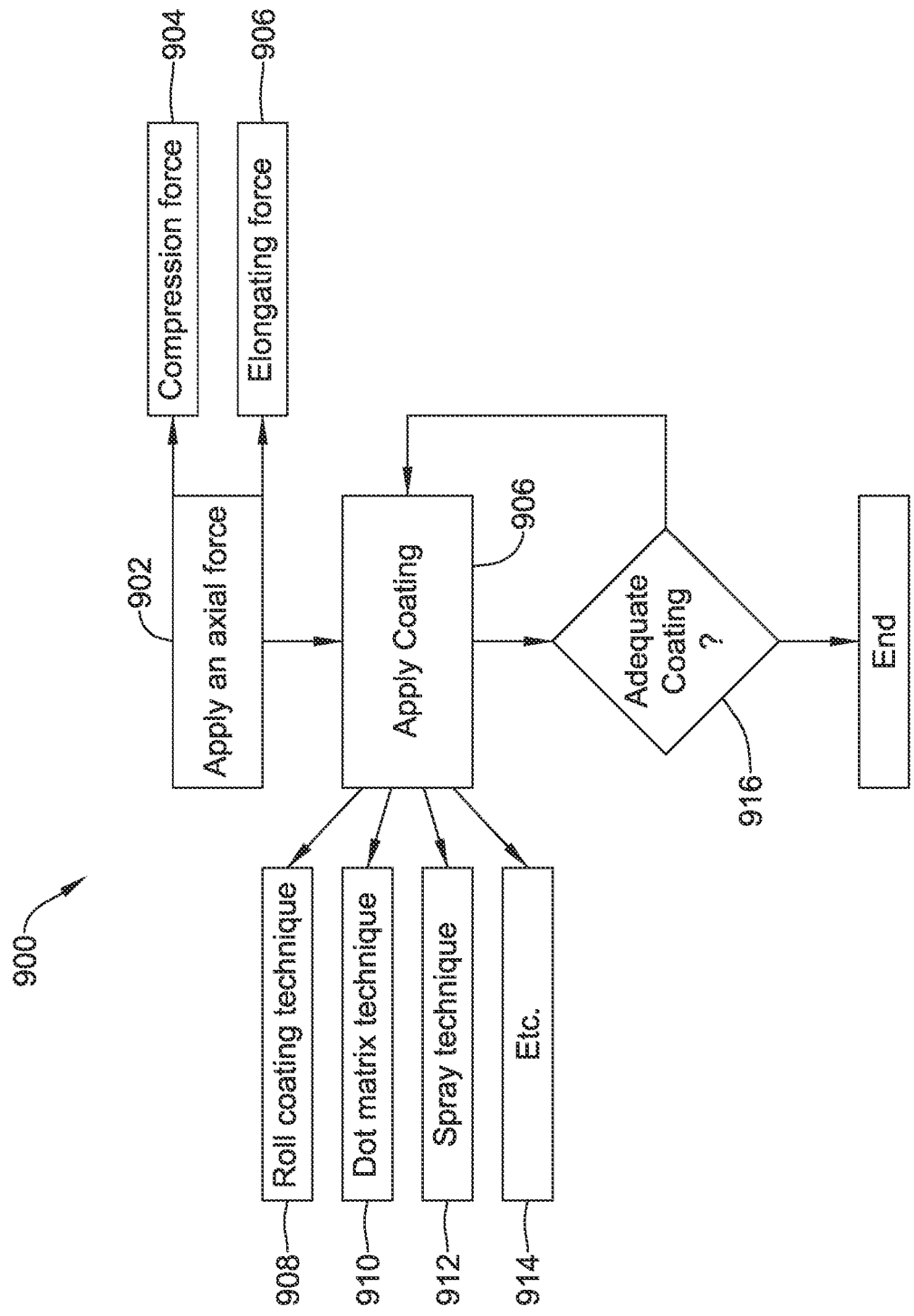
FIG. 9 is a block flow diagram for an illustrative method.

FIG. 9 depicts an illustrative flow-diagram of a method 900 of selectively coating portions of an expandable stent. In an example, a braided tubular member of the stent may be in a nominally deployed state and the method 900 may begin at step 902 where an axial force may be applied to the braided tubular member to change an axial length of the braided tubular member from the nominally deployed state. The changed length of the braided tubular member may be less than or greater than the length of the braided tubular member in the nominally deployed state. As described herein, the braided tubular member may have wires that are braided to form radially outward wire segments that are located radially outside of radially inward wire segments at crossover points along and around the braided tubular member. Moreover, the wires may cross multiple times with one another at crossover points. These crossover points may also function as pivot points and where a radially outward wire segment may pivot relative to an intersecting radially inward wire segment at each crossover point. For example, when the axial force is applied, the wires may pivot about the pivot points and alter the pivot angles between intersecting wire segments. In some cases, the pivot angles may be the measured angles in relation to a longitudinal axis (or a line segment parallel to the longitudinal axis) of the braided tubular member. In some examples, the axial force may be a compressive force 904 applied to the braided tubular member. When the compression force is applied, the pivot angles may increase, the diameter of the braided tubular member may increase, and the length of the braided tubular member may decrease, changing the braided tubular member from the nominally deployed state to an axially contracted state. In some examples, the axial force may be an elongating force 906 applied to the braided tubular member. When the elongating force is applied, the pivot angles may decrease, the diameter of the braided tubular member may decrease, and the length of the braided tubular member may increase, changing the braided tubular member from the nominally deployed state to an axially elongated state.

Once the braided tubular member is in the axially contracted state or axially elongated state, at step 906, a coating may be applied to the braided tubular member. In some examples, the coating may be applied using a roll coating technique 908. In some examples, the coating may be applied using a dot matrix coating technique 910. In some examples, the coating may be applied using a spray coating technique 912. In some examples, other coating techniques 914, such as an electrospinning technique, may be used. When applying the coating, some portions of the braided wires may be coated with the coating while other portions of the braided wires are left uncoated. The uncoated portions may be the radially inward wire segments located at the crossover points. Moreover, the uncoated length of the radially inward wire segments crossing under a radially outward wire segment at the crossover points may be greater than a diameter of the radially outward wire segment at the crossover point to allow the radially outward wire segments to pivot at the crossover points without contacting the coating on the coated portions of the intersecting braided wires at the crossover points. As a result of the coating process, each of the plurality of braided wires includes radially outward wire segments including the coating alternating with a plurality of radially inward wire segments devoid of the coating along a length of the wire.

At step 916, it may be determined whether the braided tubular member has been adequately coated. If it is determined that the braided tubular member has not been adequately coated, step 906 may be repeated. If it is determined that the braided tubular member has been adequately coated, the method 900 may end.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An implantable stent comprising:
a braided tubular member formed of a plurality of braided wires, the braided tubular member being radially expandable from a radially contracted state to a nominally deployed state, the braided tubular member including a plurality of radially outward wire segments crossing over and positioned radially outward of a plurality of radially inward wire segments at a plurality of crossover points;
wherein the radially inward wire segments contact the radially outward wire segments along a contact length of the radially outward wire segments at the crossover points in the radially contracted state, the contact length being greater than a diameter of the radially inward wire segments; and
a coating extending only partially around a circumference of the radially outward wire segments at the crossover points, such that an uncoated length of the radially outward wire segments is greater than the contact length.

2. The implantable stent of claim 1, wherein at each crossover point, the uncoated length of the radially outward wire segment faces and/or is in contact with the radially inward wire segment.

3. The implantable stent of claim 1, wherein the crossover points are maintained at a constant location along a length of the wires.

4. The implantable stent of claim 1, wherein an uncoated length of the radially inward wire segments is greater than a length of the radially inward wire segments contacting the radially outward wire segments at the crossover points when the braided tubular member is in the nominally deployed state.

5. The implantable stent of claim 4,
wherein the braided tubular member is radially compressible from the nominally deployed state to the radially contracted state; and
wherein a length of the radially inward wire segments contacting the radially outward wire segments at the crossover points in the radially contracted state is greater than the length of the radially inward wire segments contacting the radially outward wire segments at the crossover points when the braided tubular member is in the nominally deployed state.

6. The implantable stent of claim 5, wherein the radially contracted state is determined based on a pivot angle between adjacent wire segments at the crossover points.

7. The implantable stent of claim 6, wherein the pivot angle has a value between 0° and 45°.

8. The implantable stent of claim 1, wherein the radially inward wire segments are uncoated and devoid of the coating.

9. An implantable stent comprising:
a braided tubular member formed of a plurality of braided wires, the braided tubular member including a plurality of radially outward wire segments crossing over and positioned radially outward of a plurality of radially inward wire segments at a plurality of crossover points; and
a coating extending only partially over the plurality of braided wires forming coated and uncoated portions, wherein the uncoated portions include uncoated lengths of the radially inward wire segments located at and extending in opposite directions from the crossover points.

10. The implantable stent of claim 9, wherein the uncoated length of each uncoated portion of the radially inward wire segments is greater than a diameter of the radially outward wire segment at each crossover point.

11. The implantable stent of claim 9, wherein at each crossover point, a portion of the radially outward wire segment that faces and/or is in contact with the radially inward wire segment, is devoid of the coating.

12. The implantable stent of claim 11, wherein the crossover points are maintained at a constant location along a length of the wires.

13. The implantable stent of claim 9, wherein the uncoated portions include the coating extending only partially around a circumference of the radially outward wire segments at the crossover points.

14. The implantable stent of claim 9, wherein the uncoated length of the radially inward wire segments is greater than a length of the radially inward wire segments contacting the radially outward wire segments at the crossover points when the braided tubular member is in a nominally deployed state.

15. The implantable stent of claim 14,
wherein the braided tubular member is radially compressible from the nominally deployed state to a radially contracted state; and
wherein a length of the radially inward wire segments contacting the radially outward wire segments at the crossover points in the radially contracted state is greater than the length of the radially inward wire segments contacting the radially outward wire segments at the crossover points when the braided tubular member is in the nominally deployed state.

16. The implantable stent of claim 15, wherein the radially contracted state is determined based on a pivot angle between adjacent wire segments at the crossover points.

17. The implantable stent of claim 16, wherein the pivot angle has a value between 0° and 45°.

18. An implantable stent comprising:
a braided tubular member formed of a plurality of braided wires, the braided tubular member including a plurality of radially outward wire segments crossing over and positioned radially outward of a plurality of radially inward wire segments at a plurality of crossover points; and
a coating extending only partially over the plurality of braided wires forming coated and uncoated portions, wherein each of the plurality of braided wires includes coated portions of the radially outward wire segments alternating with uncoated portions of the radially inward wire segments along a length of the braided wire, wherein a length of each of the uncoated portions is greater than a diameter of the radially inward wire segments.

19. The implantable stent of claim 18, wherein a length of each of the uncoated portions of the radially inward wire segments is less than a length of each of the coated portions of the radially outward wire segments along each of the braided wires.

20. The implantable stent of claim 18, wherein at each crossover point, a portion of the radially outward wire segment that faces and/or is in contact with the radially inward wire segment, is devoid of the coating.

* * * * *